(12) United States Patent
Maezawa

(10) Patent No.: US 6,231,520 B1
(45) Date of Patent: May 15, 2001

(54) TACTILE SENSOR SIGNAL PROCESSING DEVICE CAPABLE OF OBTAINING DETAILED LIVING BODY INFORMATION IN SHORT TIME

(75) Inventor: Miyuki Maezawa, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/323,298

(22) Filed: Jun. 1, 1999

(30) Foreign Application Priority Data

Jun. 2, 1998 (JP) .................................................. 10-152427
Mar. 31, 1999 (JP) .................................................. 11-093792

(51) Int. Cl.$^7$ ........................................................ A61B 5/00
(52) U.S. Cl. .......................... 600/552; 600/587; 600/595
(58) Field of Search .................................. 600/552, 587, 600/590

(56) References Cited

U.S. PATENT DOCUMENTS

| | | | |
|---|---|---|---|
| 5,365,457 | * 11/1994 | Madigosky | 600/552 |
| 5,368,004 | * 11/1994 | Cain et al. | 600/552 |
| 5,433,211 | * 7/1995 | Brammer et al. | 600/552 |
| 5,836,876 | * 11/1998 | Dimarogonas | 600/552 |
| 5,840,041 | * 11/1998 | Petter et al. | 600/552 |
| 5,984,880 | * 11/1999 | Lander et al. | 600/595 |

FOREIGN PATENT DOCUMENTS 9-96600    4/1997  (JP) .

OTHER PUBLICATIONS

Hans L. Oestreicher; "Field and Impedance of an Oscillating Sphere in a Viscoelectric Medium with an Application to Biophysics"; Nov., 1951; pp. 707–714; Journal of the Acoustical Society of America, vol. 23, No. 6.

Henning E. von Gierke et al; "Physics of Vibrations in Living Tissues"; Nov. 8, 1951; pp. 886–900; Aero Medical Laboratory, Air Development Center, Wright–Patterson Air Force Base, Dayton, Ohio.

* cited by examiner

Primary Examiner—Cary O'Connor
Assistant Examiner—Pamela L. Wingood
(74) Attorney, Agent, or Firm—Frishauf, Holtz, Goodman, Langer & Chick, P.C.

(57) ABSTRACT

A tactile sensor signal processing device includes a tactile sensor using a piezoelectric vibrator, a resonant resistance change detect unit, a resonant frequency change detect unit, a vibrator constant storage unit, and a signal processing unit. The resonant resistance change detect unit detects a change in resonant resistance of impedance characteristics of the piezoelectric vibrator. The resonant frequency change detect unit detects a change in resonant frequency of impedance characteristics of the piezoelectric vibrator. In the vibrator constant storage unit are stored in advance physical constants that include the size of the vibrating portion of the piezoelectric vibrator, piezoelectric and coupling constants associated with the piezoelectric mode of the piezoelectric vibrator, the density of the piezoelectric vibrator, and the size of a contact which is brought into contact with a subject to apply vibrations to it. The signal processing unit computes independently each of the real part and the imaginary part of shear elastic modulus indicating the viscoelastic characteristics of the subject on the basis of the results of detection by the resonant resistance change detect unit and the resonant frequency change detect unit and the physical constants stored in the vibrator constant storage unit.

27 Claims, 10 Drawing Sheets

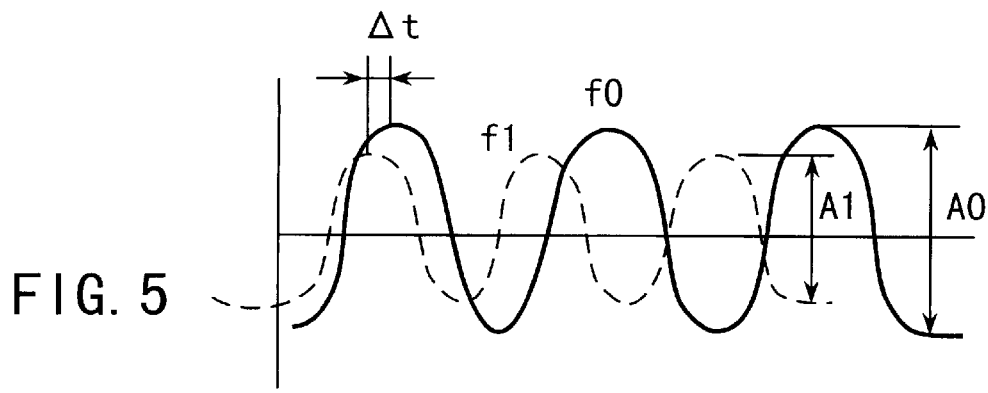
FIG. 5
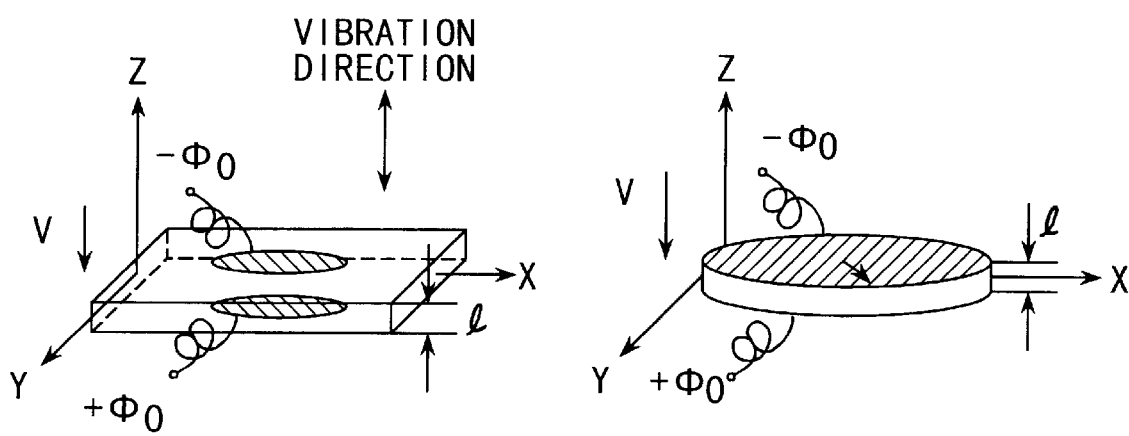
FIG. 6A
FIG. 6B
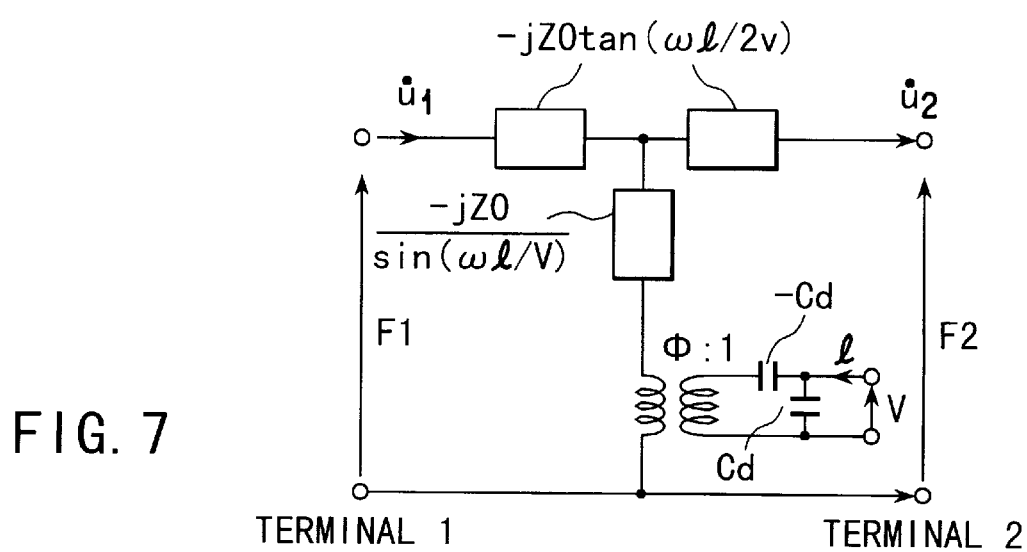
FIG. 7

TACTILE SENSOR SIGNAL PROCESSING DEVICE CAPABLE OF OBTAINING DETAILED LIVING BODY INFORMATION IN SHORT TIME

BACKGROUND OF THE INVENTION

The present invention relates to a tactile sensor that detects viscoelastic characteristics of viscoelastic subjects.

For endscopes, importance has recently been set to a function of operating on a subject under observation rather than a function as an instrument for observing the interior of a living body. Endscope-based operations, such as are exemplified by enucleation of a gallbladder, and endscope-based diagnosis are expected to spread increasingly in the future.

In perforing appropriately more complicated, elaborate operations or diagnosis/treatment within a body cavity, not only visual information but also tactile information becomes more important.

Living bodies are viscoelastic mediums. The tactile sense (the sense of touch) described herein is defined as perception of a reactive force from a viscoelastic medium. A sensor used to detect the viscoelastic characteristics of a subject is referred to as a tactile sensor.

Using complex elastic modulus G*, the viscoelastic characteristics are generally represented by $$G^* = G' + jG'' \tag{1}$$

The real part G' in the complex elastic modulus G* corresponds to the elasticity and the imaginary part G'' corresponds to the viscosity.

Using shear modulus $\mu$, the viscoelastic characteristics can also be represented by $$\mu^* = \mu_1 + j\omega\mu_2 \tag{2}$$

In living tissues, muscles and intertissue fluids are intermingled to exhibit the viscoelasticity. In morbid regions such as tumors, indurations, etc., both the real part G' and the imaginary part G'' in the complex elastic modulus G* show different values from those in normal regions.

In order to measure the complex elastic modulus G*, it is required to measure the time-varying response of a subject. One measurement method involves giving vibrations to living tissues, measuring the response from the tissues, and determining the complex elastic modulus.

The qualitative detection of the viscoelasticity in that manner through the use of a tactile sensor allows for more accurate diagnosis of morbid regions.

In view of such a need, a method is described in "Physics of Vibrations in Living Tissues" by H. E. Gierke, et al., J. Applied Physiology, 4. 886/900 (1952), which involves exciting a vibrator put on human skin, calculating a mechanical impedance from the response, and solving a mechanical impedance-related theoretical formula derived in advance to obtain the elastic coefficient $\mu_1$ and the viscosity coefficient $\mu_2$ of the skin.

In addition, as a device for measuring the viscoelastic characteristics of a living body, a tactile sensor signal processing device has been disclosed in Jpn. Pat. Appln. KOKAI publication No. 9-96600 by way example, which makes use of changes in resonant resistance and resonant frequency of a piezoelectric vibrator to separate the viscoelastic characteristics of the living body into elasticity and viscosity.

As shown in FIG. 19, this type of tactile sensor signal processing device comprises a tactile sensor 101 for detecting the viscoelastic characteristics of a subject through changes in impedance characteristics of a piezoelectric vibrator, a resonant resistance change detector 102 for detecting a change in resonance resistance of the impedance characteristics, a resonant frequency change detector 103 for detecting a change in resonant frequency, and a signal processing unit 105 for calculating the real part and the imaginary part of the complex elastic modulus indicating the viscoelastic characteristics of the subject on the basis of the results of detection by the detectors 102 and 103.

In such an arrangement, if an oscillator circuit is used which uses equivalent-circuit constants of the piezoelectric vibrator as its circuit elements, then its output signal reflects the impedance characteristics of the vibrator.

When the oscillator circuit is in the no-load state, its output signal is outputted at close to the resonant frequency $f_r$ of the piezoelectric vibrator and its amplitude depends on the resonant resistance $Z_r$ of the vibrator.

When a viscoelastic medium is attached to the oscillator, the resonant frequency becomes $f_r'$ and the resonant resistance changes to $Z_r'$.

That is, the output signal of the oscillator reflects changes in impedance characteristics of the piezoelectric vibrator.

Thus, a change in resonant frequency and a change in resonant resistance can be detected by branching the oscillator output and converting the frequency component into a voltage signal for processing in the signal processing unit 105.

The resonance resistances $Z_r'$ and $Z_r''$ detected by the resonant resistance change detector 102 and the resonant frequencies $f_r$ and $f_r'$ detected by the resonant frequency change detector 103 are entered into the signal processing unit 105 and subjected to computational processing in accordance with a procedure incorporated in advance in the signal processing unit, so that the real part G' and the imaginary part G'' of the complex elastic modulus G* are computed.

For example, if the equivalent-circuit constants ($C_1$, $L_1$, equipment constants $K_R$, $K_L$), the resonant resistance and the resonant frequency are known already, it is not until both a change in resonant frequency and a change in resonant resistance are measured that the real part G' and the imaginary part G'' of the complex elastic modulus G* can be computed. The viscoelasticity can be detected, as indicated by $$G' = \frac{f_r'^4 K_R^2 (Z_r' - Z_r)^2 - K_L^2 \omega^2 L_1^2 (f_r^2 - f_r'^2)^2}{p f_r'^4} \tag{3}$$

$$G'' = \frac{K_R^2 (Z_r' - Z_r) - K_L^2 \omega^2 L_1^2 (f_r^2 - f_r'^2)^2}{16\pi^4 C_1^2 p f_r'^4 f_r'^4} \tag{4}$$

In determining the mechanical impedance characteristics of a subject having viscoelasticity like a living body employing vibrations, it is required to keep the vibrator's state of contact with the subject unchanged or to reduce the measurement time because heartbeats cause movement of the living body.

In the conventional method by H. E. Gierke et al, the vibrator is excited with sinusoidal waves and the above-described $\mu_1$ and $\mu_2$ are computed by solving equations obtained at a limited number of typical frequencies.

Thus, this method involves a plurality of measurements for each measurement point and is subject to the constraint that the physical state of the subject to be measured must be kept stable during measurement and cannot therefore be said to be suitable for measurement in living bodies.

For the piezoelectric vibration phenomenon as in the piezoelectric vibrator, the solution must be found from an equation of motion, which is established from a piezoelectric equation so that electrical conditions are satisfied, under mechanical terminal conditions, and further the impedance and equivalent-circuit elements seen by electrical terminals must be determined from the electrical conditions.

The previously described tactile sensor signal processing device disclosed in Jpn. Pat. Appln. KOKAI Publication No. 9-96600, which computes the complex elastic modulus using the equipment constants $K_R$ and $K_L$ for converting the electrical impedance of a viscoelastic medium to the mechanical impedance, is difficult to use to compute the viscoelasticity accurately because the displacement direction of the piezoelectric vibrator elements, the excitation electric field and the mechanical terminal conditions are not taken into account.

In addition, there are problems with the equipment constants $K_R$ and $K_L$ in that they must be computed in advance on the basis of measurements of the impedance characteristic and their values vary from viscoelastic medium to viscoelastic medium.

BRIEF SUMMARY OF THE INVENTION

It is an object of the present invention to provide a tactile sensor signal processing device which allows more detailed biological information to be obtained in a short time taking into consideration a measurement time, two or more measurements at the same point, a displacement direction, electric field, mechanical conditions and electrical conditions of a piezoelectric vibrator used.

To achieve the above object, according to an aspect of the present invention, there is provided a tactile sensor signal processing device for detecting viscoelastic characteristics of a subject through changes in impedance characteristics of a vibrator, comprising: a tactile sensor using a piezoelectric vibrator; resonant resistance change detecting means for detecting a change in resonant resistance of the impedance characteristics of the piezoelectric vibrator; resonant frequency change detecting means for detecting a change in resonant frequency of the impedance characteristics of the piezoelectric vibrator; vibrator constant storaging means for prestoring physical constants including a size of a vibrating portion of the piezoelectric vibrator, piezoelectric and coupling constants associated with a piezoelectric phenomenon of the piezoelectric vibrator, density of the piezoelectric vibrator, and a size of a contact that is pressed against the subject for applying vibrations to it; and signal processing means responsive to results of detection by the resonant resistance change detecting means and the resonant frequency change detecting means, and the physical constants stored in the vibrator constant storaging means for independently computing real and imaginary parts of shear elastic modulus indicating the viscoelastic characteristics of the subject.

According to another aspect of the present invention, there is provided a tactile sensor signal processing device for detecting viscoelastic characteristics of a subject through changes in impedance characteristics of a vibrator, comprising: a tactile sensor using a piezoelectric vibrator; resonant resistance change detect means for detecting a change in resonant resistance of the impedance characteristics of the piezoelectric vibrator; resonant frequency change detect means for detecting a change in resonant frequency of the impedance characteristics of the piezoelectric vibrator; vibrator constant storage means for prestoring constants involved in computation of shear elastic modulus indicating the viscoelastic characteristics of the subject; and signal processing means responsive to the results of detection by the resonant frequency change detect means and the resonant resistance change detect means and the constants stored in the constant storage means for computing independently each of the real part $\mu_1$ and the imaginary part $\mu_2$ of the shear elastic modulus of the subject on the basis of the following two expressions:

$$df = L + M \times \Delta F^N \tag{5}$$

where $\Delta F$ is the change in oscillating frequency, $dZ$ is the change in resonant resistance, $df$ is the change in resonant frequency, and L, M and N are constants, and $$dZ = R \times \Delta A + S \tag{6}$$

where $\Delta A$ is the change in amplitude, $dZ$ is the change in resonant resistance, and R and S are constants.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 shows output waveforms of the oscillator of FIG. 2;

FIGS. 6A and 6B show a piezoelectric vibrator in thickness longitudinal mode and its associated coordinate system, respectively;

FIG. 7 shows a Maison equivalent circuit in which forces on the front and back sides of the piezoelectric vibrator are sought as $F_1$ and $F_2$;

DETAILED DESCRIPTION OF THE INVENTION

Figure 1:
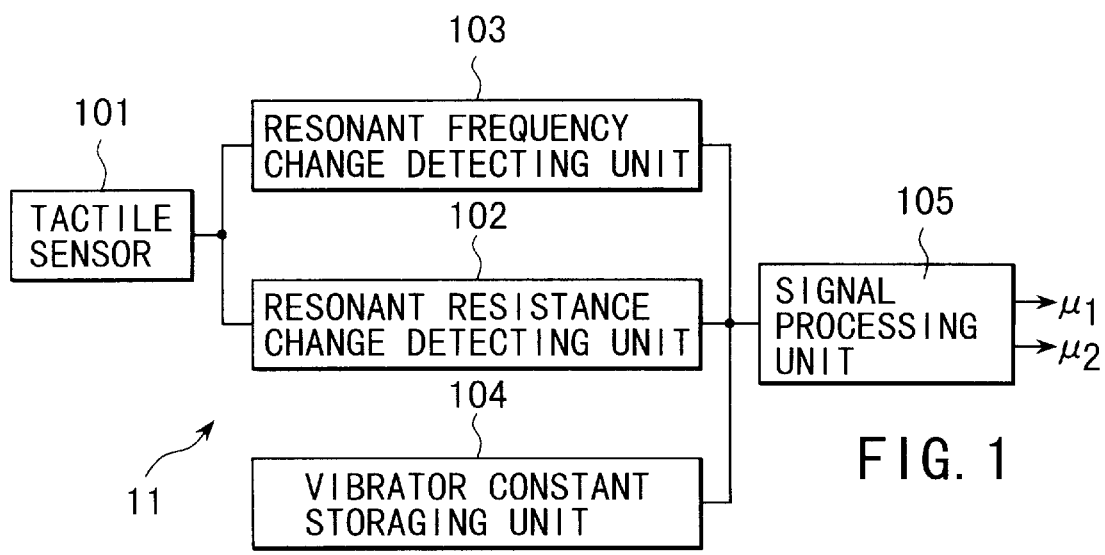
FIG. 1 is a schematic representation of a tactile sensor signal processing device according to a first embodiment of the present invention.

Reference will now be made in detail to the presently preferred embodiments of the invention as illustrated in the accompanying drawings, in which like reference characters designate like or corresponding parts throughout the several drawings.

First Embodiment

First, description will be given of the arrangement, workings and advantages of a first embodiment of a tactile sensor signal processing device of the present invention.

FIG. 1 is a schematic representation indicated by main construction units of the tactile sensor signal processing device 11 of the first embodiment.

The tactile sensor signal processing device 11 is constructed from a tactile sensor 101 which detects the viscoelastic characteristics of a subject under examination using changes in impedance characteristics of a piezoelectric vibrator 201 (see FIG. 2A), a resonant resistance change detecting unit 102 which detects a change in resonant resistance of the impedance characteristics of the piezoelectric vibrator, a resonant frequency change detecting unit 103 which detects a change in resonant frequency of the impedance characteristics of the piezoelectric vibrator, a vibrator constant storage unit 104 in which physical constants of the piezoelectric vibrator are stored in advance, and a signal processing unit 105 which is responsive to the physical constants stored in the storaging unit 104 and the results of detection by the resonant resistance change detecting unit 102 and the resonant frequency change detecting unit 103 to compute independently each of the real part and the imaginary part of the shear viscoelastic modulus as the viscoelastic characteristics of the subject.

Figure 2A:
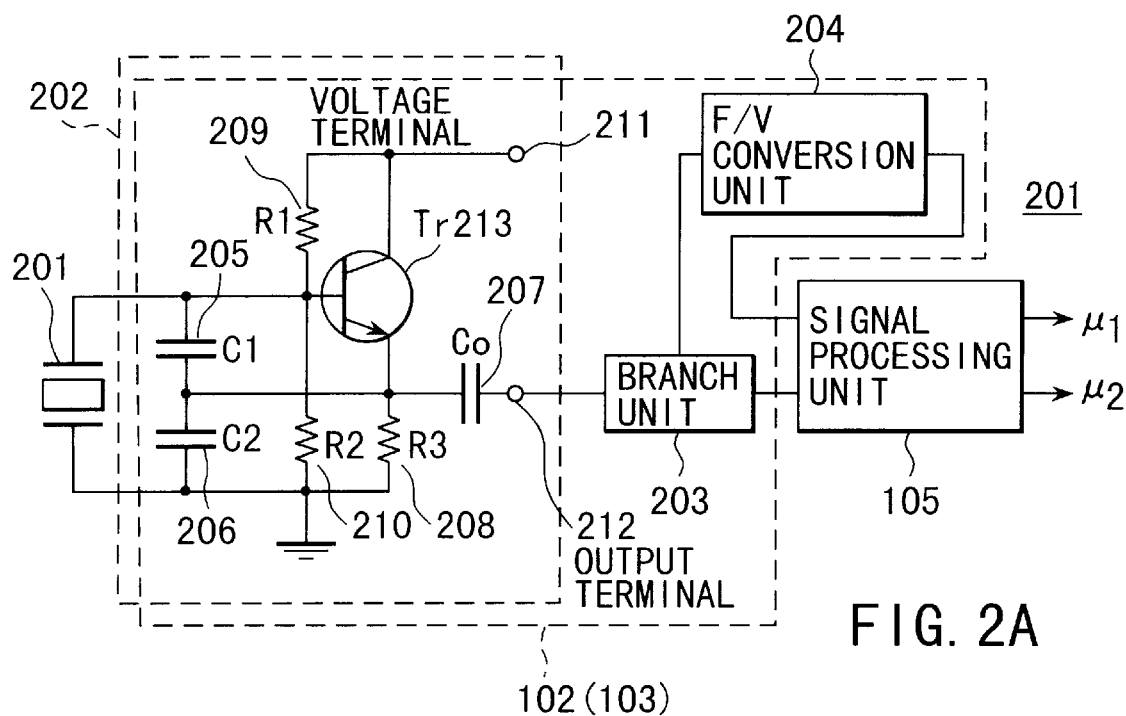
FIG. 2A shows specific circuit arrangements of the tactile sensor, the resonance resistance change detecting unit, and the resonance frequency change detecting unit of FIG. 1.

FIG. 2A illustrates a specific circuit arrangement of the resonant resistance change detecting unit 102 and the resonant frequency change detecting unit 103.

This circuit arrangement comprises an oscillator circuit 202 coupled to a piezoelectric vibrator 201, a branch unit 203 that branches an oscillation output of the oscillator circuit, and an F/V conversion unit 204 that subjects one of the branched outputs to frequency to voltage conversion.

Figure 2B:
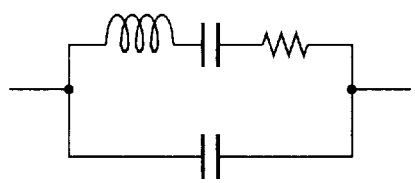
FIG. 2B shows an equivalent circuit of the piezoelectric vibrator of FIG. 1.

FIG. 2B shows an equivalent circuit of the piezoelectric vibrator 201.

The oscillator circuit 202 consists of a Colpitt's oscillator that uses as its circuit element the piezoelectric vibrator 201 the equivalent circuit of which is shown in FIG. 2B.

The oscillator circuit 202 comprises a capacitor ($C_1$) 205, a capacitor ($C_2$) 206, a capacitor ($C_0$) 207, a resistor ($R_3$) 208, a resistor ($R_1$) 209, a resistor ($R_2$) 210, a voltage terminal 211, a voltage terminal 212, and a transistor (Tr) 213.

Figure 3:
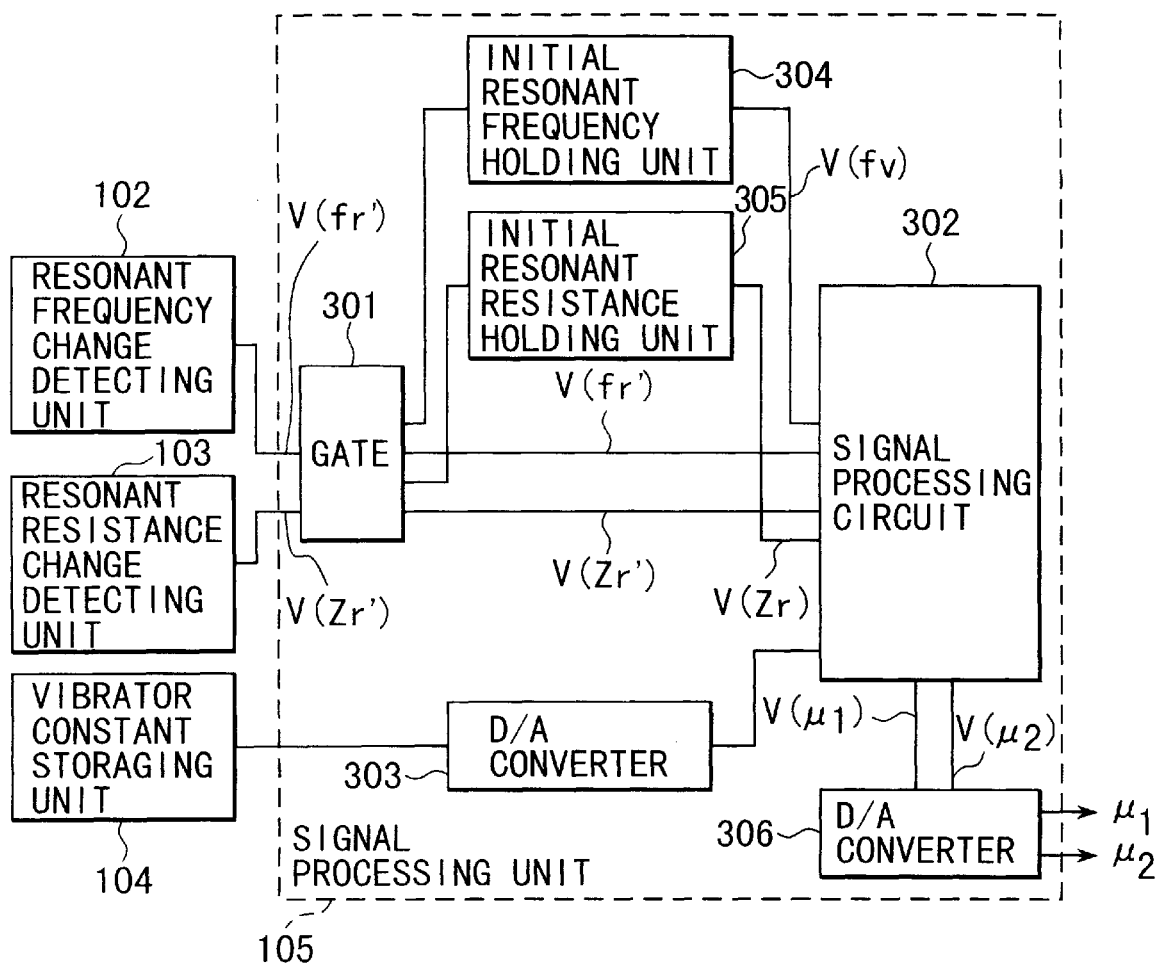
FIG. 3 is a block diagram of the signal processing unit of FIG. 1.

FIG. 3 illustrates a specific circuit arrangement of the signal processing unit 105.

The signal processing unit 105 shown in FIG. 3 is connected to receive an output signal $V(Z_r')$ indicative of the resonant resistance $Z_r'$ detected by the resonant resistance change detecting unit 102 arranged as shown in FIG. 2A, an output signal $V(f_r')$ indicative of the resonant frequency $f_r'$ detected by the resonant frequency change detecting unit 103 likewise arranged as shown in FIG. 2A, and output data from the vibrator constant storaging unit 104.

The signal processing device shown in FIG. 3 comprises a gate 301 which takes in the output signals $V(Z_r')$ and $V(f_r')$ at the same time, an initial resonant frequency hold unit 304 which holds the resonant frequency at no-load time, an initial resonant resistance holding unit 305 which holds the resonant resistance at no-load time, a signal processing circuit 302, a D/A converter 303, and an A/D converter 306.

The output signal $V(Z_r')$ indicative of the resonant resistance $Z_r'$ from the resonant resistance change detecting unit 102 and the output signal $V(f_r')$ indicative of the resonant frequency $f_r'$ from the resonant frequency change detecting unit 103 are taken in by the gate 301 at the same time and then fed into the signal processing circuit 302.

The resonant frequency $f_r$ and the resonant resistance $Z_r$ to which reference is made are stored into the initial resonant frequency hold unit 304 and the initial resonant resistance hold unit 305, respectively, prior to measurement and fed into the signal processing circuit 302 when necessary.

The output data of the vibrator constant storage unit 104 is converted into a direct-current voltage signal V, i.e., an analog signal, through the D/A converter 303 and then applied to the signal processing circuit 302.

Figure 4:
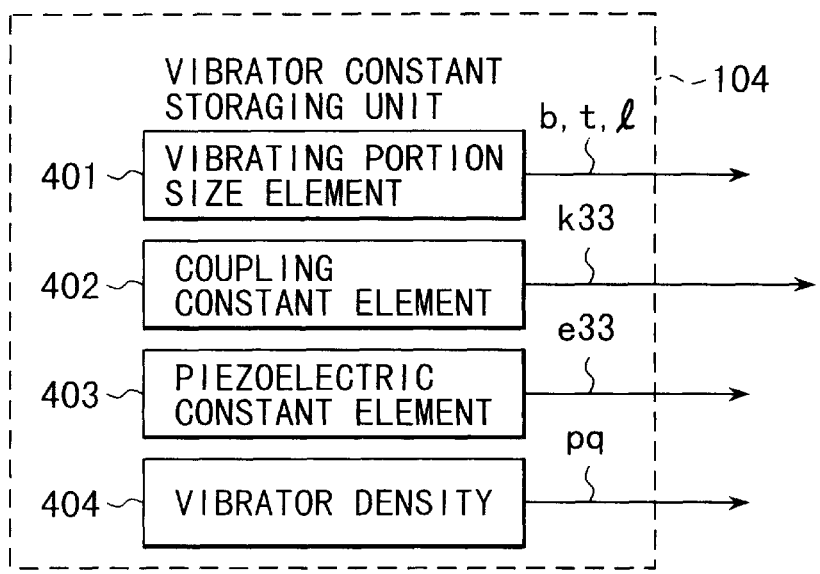
FIG. 4 shows a specific configuration of the vibrator constant storage unit of FIG. 1.

FIG. 4 illustrates a specific arrangement of the vibrator constant storaging unit 104.

The constants stored in the vibrator constant storage unit include a vibrator size element 401 indicating the dimensions of the vibrating portion of the vibrator, a vibrator coupling constant element 402, a vibrator elastic constant element 403, and a density element 404 of the vibrator.

These elements are fed through the D/A converter 303 into the signal processing circuit 302 in computing the real part $\mu_1$ and the imaginary part $\mu_2$ of the shear elastic modulus $\mu^*$ of a viscoelastic medium.

The workings of the above arrangement will be described hereinafter.

FIG. 5 shows waveforms of output signals of the oscillator circuit 202 arranged as shown in FIG. 2A.

The use of the oscillator circuit 202 that uses the equivalent-circuit constants of the piezoelectric vibrator 201 as its circuit elements allows its output signal to be a reflection of the impedance characteristics of that vibrator.

At no-load time, the output signal of the oscillator circuit 202 has a frequency close to the resonant frequency $f_0$ of the piezoelectric vibrator 201 as indicated by a solid line in FIG. 5 and its amplitude $A_0$ is associated with the resonant resistance of the piezoelectric vibrator.

When the oscillator is coupled with a viscoelastic medium, the output signal of the oscillator circuit 202 is outputted at a frequency $f_1$ as indicated by a dotted line in FIG. 5 and its amplitude changes from $A_0$ to $A_1$.

Thereby, the resonant resistance change detecting unit 102 and the resonant frequency change detecting unit 103 can detect a change in resonant resistance and a change in resonant frequency, respectively, by branching the output signal of the oscillator circuit 202 and converting a frequency component into a voltage signal for processing in the signal processing unit 105.

The resonant resistance $Z_r$ thus detected by the resonant resistance change detecting unit 102 and the resonant frequency $f_r$ detected by the resonant frequency change detecting unit 103 are fed into the signal processing circuit 105 together with the numerical values stored in advance in the vibrator constant storage unit 104.

The signal processing unit 105 then performs operations on the input data in accordance with the procedure incorporated in advance to compute the real part $\mu_1$ and the imaginary part $\mu_2$ of the shear elastic modulus $\mu^*$ indicating the viscoelastic characteristics of the subject.

The computational procedure in this case will be described next.

FIGS. 6A and 6B show a piezoelectric vibrator in the thickness longitudinal mode and its associated coordinate system.

The vibrator shown in FIG. 6A is of an energy confinement type of such structure that circular electrodes are provided in the center of the front and back sides of the vibrator.

With the vibrator of this structure, it is only electrode portions that cause vibrations.

The vibrator is polarized in the direction of thickness and the direction of longitudinal vibrations is coincident with the direction of polarization. By an electric field along the Z-axis direction, only the electrode portions as shown in FIG. 6B are subjected to expansion vibrations in the Z-axis direction.

Piezoelectric equations in this case are given by $$T_3 c_{33}^E S_3 - e_{33} E_3 \quad (7)$$

$$D_3 = e_{33} S_3 + \varepsilon_{33}^S E_3 \quad (8)$$

where T is the stress, $S_3$ is the distortion, $c_{33}^E$ is the elastic constant, $e_{33}$ is the piezoelectric constant, and $\varepsilon_{33}^S$ is the dielectric constant.

Letting the vibration displacement in the Z-axis direction be u in the thickness longitudinal mode yields $$S_3 = \frac{\partial u}{\partial Z} \quad (9)$$

$$E_3 = -\frac{\partial \varphi}{\partial Z} \quad (10)$$

The equation of motion becomes $$\rho_q \frac{\partial^2 u}{\partial t^2} = c_{33}^D \frac{\partial^2 u}{\partial Z^2} - \frac{e_{33}}{\varepsilon_{33}^S} \frac{\partial D_3}{\partial Z} \quad \because divD = 0 \quad (11)$$

where $\rho_q$ is the density of the piezoelectric vibrator.

By solving this equation and letting the current I flowing between the electrodes be $$I = j\omega \int\int D_3 dx dy \quad (12)$$

and the forces at the front and back sides be $F_1$ and $F_2$, the Maison's electrical equivalent circuit is found to become as shown in FIG. 7.

In the equivalent circuit shown in FIG. 7, there are two acoustic terminals 1 and 2.

Consider now a case where the acoustic terminal 1 is short-circuited and an acoustic impedance $Z_3$ is coupled to the acoustic terminal 2.

The acoustic impedance $Z_3$ corresponds to the acoustic impedance to which the longitudinally vibrating piezoelectric vibrator serving as a tactile sensor is subjected when brought into contact with a subject.

Figures 8A, 8B:
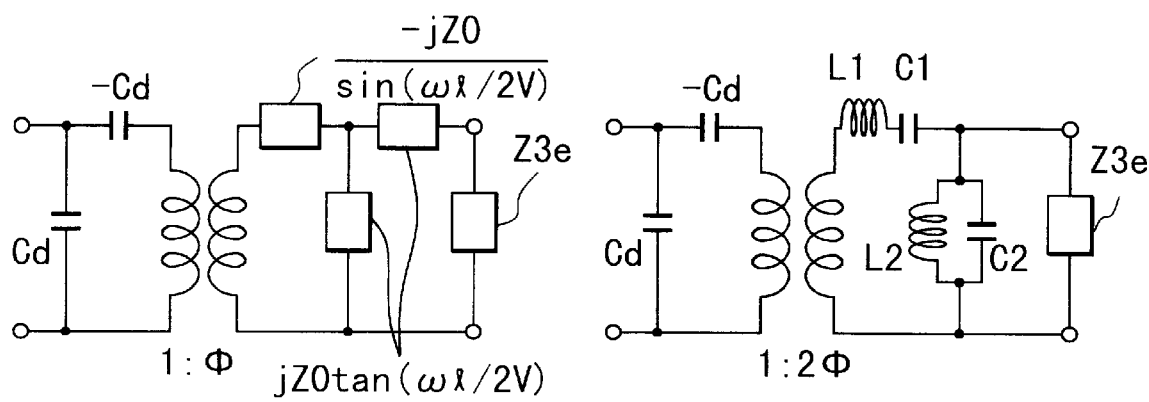
FIGS. 8A and 8B show situations in which an electrical impedance $Z_{3e}$ corresponding to an acoustic impedance $Z_3$ is connected to the equivalent circuit shown in FIG. 7.

In FIGS. 8A and 8B, $Z_{3e}$ is an electrical impedance.

In the case of longitudinal mode, the current I at electrical terminals and the input admittance $Y_f$ are related by $$I = j\omega\left(\frac{\varepsilon_{33}^S \pi a^2}{l}\right)(-V) + j\omega \frac{e_{33}\pi a^2}{l} \tan\left(\frac{\omega l}{2v}\right) \times \quad (13)$$

$$\frac{e_{33}(-V)}{c_{33}^D\left(\frac{\omega l}{2v}\right)} \frac{1}{\left\{1 - \frac{e_{33}^2}{\varepsilon_{33}^S c_{33}^D} \frac{\tan\left(\frac{\omega l}{2v}\right)}{\left(\frac{\omega l}{2v}\right)}\right\}}$$

$$Y_f = \left(\frac{-I}{V}\right) = j\omega\left(\frac{\varepsilon_{33}^S \pi a^2}{l}\right) + \quad (14)$$

$$j\frac{e_{33}^2 \pi a^2}{c_{33}^D} \frac{2}{\left(\frac{l^2}{v}\right)} \frac{1}{\cot X - \frac{k_{33}^2}{X}}$$

$$X = \frac{\omega l}{2v} \quad (15)$$

$$k_{33}^2 = \frac{e_{33}^2}{\varepsilon_{33}^S c_{33}^D} (= k_t^2) \quad (16)$$

where $k_{33}$ is the coupling constant in this case.

Resonance conditions with $Y_f = \infty$ are found to be $$\frac{\tan X}{X} = \frac{1}{k_{33}^2} \quad (17)$$

$$X = \frac{\omega l}{2v} \quad (18)$$

$$V = \sqrt{\frac{c_{33}^D}{\rho_q}} \quad (19)$$

$$C_{33}^E = (1 - k_{33}^2)C_{33}^D \quad (20)$$

Next, consider the $Y_f$ equivalent circuit using the Norton transformation and the Mittag-Leffler theorem to simplify the impedance on the secondary side of FIG. 7.

Changing $Y_f$ yields $$Y_f = j\omega\left(\frac{\varepsilon_{33}^S \pi a^2}{l}\right) + j\frac{e_{33}^2 \pi a^2}{\rho_q\left(\frac{c_{33}^D}{\rho_q}\right)}\left(\frac{l^2}{V}\right)\frac{2}{\cot X - \frac{k_{33}^2}{X}} \quad (21)$$

$$= j\omega C_d + \frac{1}{-\frac{1}{j\omega C_d} + \frac{1}{j\tan\left(\frac{\omega l}{2V}\right)\frac{2\pi a^2 e_{33}^2}{\rho_q V l^2}}}$$

$$= j\omega C_d + \frac{1}{-\frac{1}{j\omega C_d} + \frac{1}{Y'_m}}$$

Since $$Y'_m = j\omega\frac{\tan\left(\frac{\omega l}{2V}\right)\pi a^2}{\left(\frac{\omega l}{2V}\right)\rho_q l V^2} = j\omega C_d k_{33}^2 \frac{\tan X}{X} \quad (22)$$

equation (22) can be represented by $$Y_f = \frac{j\omega C_d}{1 - k_{33}^2 \frac{\tan X}{X}} \quad (23)$$

Thus, such an equivalent circuit as shown in FIG. 8A can be deduced.

Also, $$C_d = \frac{\varepsilon_{33}^S \pi a^2}{l} \quad (24)$$

$$Y_m = -\frac{1}{j\omega C_d} \quad (25)$$

Measuring the circuits in FIGS. 8A and 8B at a sufficiently low frequency results in $$Yf = \frac{j\omega C_d}{1 - k_{33}^2} \quad (26)$$

$$= j\omega(C_d + C')$$

Thus, $$C' = C_d \frac{k_{33}^2}{1 - k_{33}^2} \quad (27)$$

Here, consider an equivalent circuit at close to the point of resonance.

$Y_m$ in the above equation resonates when $\tan(\omega l/2v)=\infty$, that is, at frequencies of $\omega_r = n\pi v/l$ (n=1, 3, 5 ... ).

Consider now the fundamental resonant frequency $\omega_r = \pi v/l$ (n=1).

In the neighborhood of this point of resonance, when $Z_m$ is expanded to $$Z_m = \frac{1}{Y_m} = j\omega L + \frac{1}{j\omega C} \quad (28)$$

the relationships given by $$\left(\frac{\partial Z_m}{\partial \omega}\right)\bigg|_{\omega=\omega_r} = 0 \quad \therefore j2L = j\frac{2}{\omega_r^2 C} \quad (29)$$

$$C_{33}^E = (1 - k_{33}^2)C_{33}^D \quad (30)$$

provide $$C = \frac{8}{\pi^2}C' = \frac{8}{\pi^2}C_d \frac{k_{33}^2}{1 - k_{33}^2} \quad (31)$$

$$L = \frac{1}{\omega_r^2 C} = \frac{1}{\left(\frac{\pi}{l}\sqrt{\frac{c_{33}^D}{\rho_q}}\right)^2}\frac{1}{C} \quad (32)$$

Thus, L, C and $Z_{3e}$ are $$C = \frac{8e_{33}^2 \pi a^2}{c_{33}^E l \pi} \quad (33)$$

$$L = \frac{1}{\omega_r^2 C} = \frac{\rho_q l^3 (1 - k_{33}^2)}{8e_{33}^2 \pi a^2} \quad (34)$$

$$Z_{3e} = \frac{Z_3}{4}\frac{1}{e_{33}^2 l^2} \quad (35)$$

Next, the mechanical impedance of a viscoelastic medium will be described using a Voigt model which, when subjected to a constant load, has its rate of elongation gradually decreasing to zero and reaches a point of equilibrium.

According to "Field and Impedance of an Oscillating Sphere in a Viscoelastic Medium with an Application to Biophysics" by H. L. Oeastreicher et al., J. Acoust. Soc. America, 23, 6, 707/714 (1951), the acoustic impedance to which a sphere is subjected when it is oscillating in contact with a semi-infinite viscoelastic medium of a Voigt model of viscoelasticity is represented by $$Z = \frac{P}{j\omega u} = \frac{4}{3}\pi\rho\omega a^3 j \times \quad (36)$$

$$\frac{\left(1 - \frac{3j}{ah} - \frac{3}{a^2 h^2}\right) - 2\left(\frac{j}{ah} + \frac{1}{a^2 h^2}\right)\left(3 - \frac{a^2 k^2}{akj + 1}\right)}{\left(\frac{j}{ah} + \frac{1}{a^2 h^2}\right)a^2\frac{k^2}{akj + 1} + \left(2 - \frac{a^2 k^2}{akj + 1}\right)}$$

$$h = \left(\frac{\rho\omega^2}{\mu}\right)^{\frac{1}{2}} \quad (37)$$

$$k = \left(\frac{\rho\omega^2}{2\mu + \lambda}\right)^{\frac{1}{2}} \quad (38)$$

$$\mu = \mu_1 + j\omega\mu_2 \quad (39)$$

$$\lambda = \lambda_1 + j\omega\lambda_2 \quad (40)$$

Z is the mechanical impedance.

Here, ρ is the density, p is the force the sphere exerts on the viscoelastic medium, a is the diameter of the oscillating sphere, $\mu_1$ is the real part of shear modulus, $\mu_2$ is the imaginary part, $\lambda_1$ is the volume compressibility, and $\lambda_2$ is the volume viscosity.

When the vibrating portion of the piezoelectric vibrator is not sphere but shaped like a disk as shown in FIGS. 6A and 6B, the above equation is changed as follows:

$$Z = \frac{P}{j\omega u} = \pi\rho\omega a^2 lj \times \quad (41)$$

$$\frac{\left(1 - \frac{3j}{ah} - \frac{3}{a^2h^2}\right) - 2\left(\frac{j}{ah} + \frac{1}{a^2h^2}\right)\left(3 - \frac{a^2k^2}{akj+1}\right)}{\left(\frac{j}{ah} + \frac{1}{a^2h^2}\right)a^2\frac{k^2}{akj+1} + \left(2 - \frac{a^2k^2}{akj+1}\right)}$$

This equation is used as mechanical acoustic impedance $Z_3$.

Silicone rubber and living muscles as viscoelastic mediums are of incompressibility with $\mu_1 \ll \lambda_1$.

From the above, $\mu_1/\lambda_1$ is set to approximately 0.

Thus, the acoustic impedance $Z_3$ becomes $$Z_3 = \frac{1}{2}a^2 l\pi\rho\omega j\left(1 - \frac{9j}{ah} - \frac{9}{a^2h^2}\right) \quad (42)$$

$$h = \omega\left(\frac{\rho}{\mu_1 + j\omega\mu_2}\right) \quad (43)$$

The expansion of equation (42) into real and imaginary parts results in $$Z_{real} = \frac{1}{2}l\pi\{9\mu_2 + 9a\rho\sqrt{\text{Abs}(\mu_1 + j\omega\mu_2)} \cos\left[0.5 \text{ Arg}\left(\frac{\rho}{\mu_1 + j\omega\mu_2}\right)\right]\} \quad (44)$$

$$Z_{imag} = \quad (45)$$

$$\frac{1}{2}l\pi\{\frac{9\mu_1}{\omega}a^2\rho + 9a\rho\sqrt{\text{Abs}(\mu_1 + j\omega\mu_2)} \sin\left[0.5 \text{ Arg}\left(\frac{\rho}{\mu_1 + j\omega\mu_2}\right)\right]\}$$

Substitution of the equation for real part $Z_{real}$ into the equation for $Z_{3e}$ yields an impedance change dZ:

$$dz = \frac{9}{8}\frac{\pi}{le_{33}^2}\{\mu_2 + a\rho\sqrt{\text{Abs}(\mu_1 + j\omega\mu_2)} \sin\left[0.5 \text{ Arg}\left(\frac{\rho}{\mu_1 + j\omega\mu_2}\right)\right]\} \quad (47)$$

A frequency change dL is obtained by substituting the equation for imaginary part Zimag into the equation for $Z_{3e}$ as follows:

$$dL = \frac{1}{8}\frac{\pi}{le_{33}^2}\{\frac{9\mu_1}{\omega}a^2\rho + \quad (47)$$

$$9a\rho\sqrt{\text{Abs}(\mu_1 + j\omega\mu_2)} \sin\left[0.5 \text{ Arg}\left(\frac{\rho}{\mu_1 + j\omega\mu_2}\right)\right]\}$$

Since the resonant frequency of the vibrator in the no-load state is $$f_r = \frac{1}{2\pi\sqrt{LC}} \quad (48)$$

a change in resonant frequency df is given by $$df = -\frac{1}{2\pi\sqrt{LC}}d\frac{L}{2L} = -f_r d\frac{L}{2L} \quad (49)$$

It is assumed here that $dL \ll L$.

$$df = \frac{1}{2}fr\frac{a^2\pi^2}{l^4\rho_q(k_{33}-1)}\{\frac{9\mu_1}{\omega} - a^2\rho\omega + \quad (50)$$

$$9a\rho\sqrt{\text{Abs}(\mu_1 + j\omega\rho_2)} \sin\left[0.5 \text{ Arg}\left(\frac{\rho}{\mu_1 + j\omega\mu_2}\right)\right]\}$$

When the oscillating frequency of the piezoelectric vibrator is so high that $\omega\mu_2 \gg \mu_1$, dZ and df become $$dz = \frac{9}{8}\frac{\pi}{le_{33}^2}(\mu_2 + a\rho\sqrt{\omega\mu_2} \cos[0.5 \text{Tan}^{-1}(\omega)]) \quad (51)$$

$$df = \frac{1}{2}fr\frac{a^2\pi^2}{l^4\rho_q(k_{33}-1)}\{\frac{9\mu_1}{\omega} - a^2\rho\omega + \quad (52)$$

$$9a\rho\sqrt{\omega\mu_2} \sin[0.5 \text{Tan}^{-1}(\omega)]\}$$

Putting A as $$A = \cos[0.5 \text{Tan}^{-1}(\omega)] = \sin[0.5 \text{Tan}^{-1}(\omega)] \quad (53)$$

and solving the above equation for the real part $\mu_1$ and the imaginary part $\mu_2$ of shear modulus which are the elasticity $\mu_1$ and the viscosity $\mu_2$, respectively, of a subject which are solutions of the equations for dZ and df yields $$\mu_1 = \frac{\omega}{18a^2\pi^2 f_r}\{2a^4\pi^2\rho\omega^2 f_r + 9a^4 A^2\pi^2\rho^2\omega^2 f_r - \quad (54)$$

$$3a^3 A\pi^{3/2}\rho\omega^{3/2}\sqrt{9a^2 A^2\pi\rho^2\omega + 32dZ_3 e le_{33}^2 f_r} +$$

$$4dfl^4\rho_q\omega(k_{33}-1)\}$$

$$\mu_2 = -\frac{1}{18\pi}\{-9a^2 A^2\pi\rho^2\omega - 16dZ_{3e}le_{33}^2 - \quad (55)$$

$$2aA\rho\sqrt{\pi\omega}\sqrt{9a^2 A^2\pi\rho^2\omega + 32dZ_{3e}le_{33}^2}$$

The equation for the imaginary part $\mu_2$ of shear modulus contains the impedance (resonant resistance) change dZ alone. This shows that the imaginary part $\mu_2$ of shear modulus has a one-to-one correspondence with the impedance (resonant resistance) change dZ.

On the other hand, the determination of the real part $\mu_1$ of shear modulus requires both the resonant frequency change df and the impedance (resonant resistance) change dZ.

If, therefore, the density $\rho_q$ of the piezoelectric vibrator, the dimensions a and l of the vibrating portion, the piezoelectric constant $e_{33}$, the coupling constant $k_{33}$, and the resonant frequency $f_r$ at no-load time are already known, it is not until both the resonant frequency change and the resonant resistance change are measured that the detection of the viscoelastic characteristics becomes possible.

FIGS. 3 and 4 show the signal processing unit based on the above computational expressions.

The above-described first embodiment allows the signal processing unit shown in FIG. 3 to compute the real part $\mu_1$ and the imaginary part $\mu_2$ of shear modulus based on the piezoelectric phenomenon of the piezoelectric vibrator.

The living tissues exhibit the viscoelastic characteristics as the result of muscles and intertissue fluids being interwined with one another. In morbid regions such as tumors and indurations, both the real part $\mu_1$ and the imaginary part $\mu_2$ of the shear viscoelastic coefficient $\mu$ change. More detailed biological information can be obtained by detecting the viscoelastic characteristics separately using the piezoelectric phenomenon of the piezoelectric vibrator as in this embodiment.

By the use of such an oscillator circuit 202 as shown in FIG. 2A, changes in impedance characteristics of the piezoelectric vibrator can be measured in real time to reduce the time required to measure the viscoelastic characteristics.

This embodiment can be modified variously. For example, even with the transverse mode in which the displacement direction of a piezoelectric vibrator is perpendicular to an excitation electric field, signal processing unit can be implemented which is adapted to compute the real part $\mu_1$ and the imaginary part $\mu_2$ of shear modulus based on the piezoelectric phenomenon in the transverse mode by selecting optimum piezoelectric and elastic constants, establishing an piezoelectric equation for the transverse mode, and solving the equation under mechanical terminal conditions and electrical conditions.

That is, even if different types of piezoelectric vibrators are used, any signal processing unit can be used, provided that it is arranged to compute the real part $\mu_1$ and the imaginary part $\mu_2$ of the shear modulus based on the piezoelectric phenomenon that take place.

Here, the transverse mode includes the thickness slip mode, the thickness expansion mode, and the thickness shear mode.

In addition, even with the bar longitudinal mode and the bar transverse mode (the bar slip mode, bar expansion mode, or bar shear mode) as well, signal processing unit can be implemented which computes the real part $\mu_1$ and the imaginary part $\mu_2$ of the shear elastic modulus based on the piezoelectric phenomenon in a similar manner to that described above.

As the oscillator circuit 202, any type of oscillator can be used, provided that it is capable of self-oscillation using the equivalent-circuit constants of the piezoelectric vibrator 201.

As the resonant frequency change detecting unit and the resonant resistance change detecting unit, use may be made of an impedance measurement instrument, which is directly connected to the piezoelectric vibrator 201.

Moreover, the piezoelectric vibrator may be shaped into other forms than a rectangular plate as used in this embodiment.

Figure 9A:
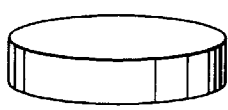
FIGS. 9A through 9H show various possible shapes of the piezoelectric vibrator.
Figure 9B:
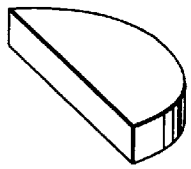
Figure 9C:
Figure 9D:
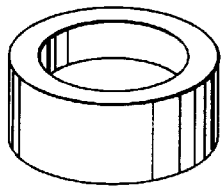
Figure 9E:
Figure 9F:
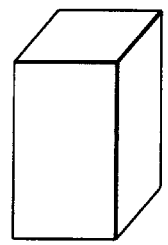
Figure 9G:
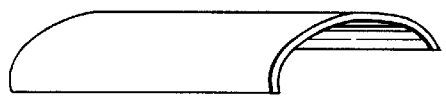
Figure 9H:
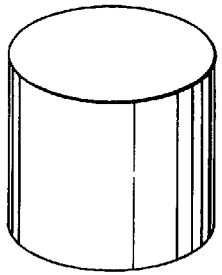

For example, the vibrator may be formed in the shape of a disk as shown in FIG. 9A, a semi-disk as shown in FIG. 9B, a ring as shown in FIG. 9C, a hollow cylinder as shown in FIG. 9D, a semi-sphere as shown in FIG. 9E, a rectangular prism as shown in FIG. 9F, a semi-drainpipe as shown in FIG. 9G, or a solid cylinder as shown in FIG. 9H.

Furthermore, although the piezoelectric vibrator used in this embodiment is of an energy confinement type, it may take other forms.

Figure 10:
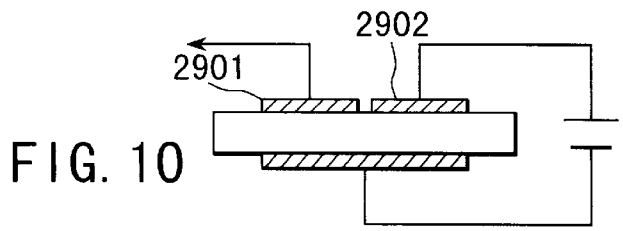
FIG. 10 shows a three-electrode piezoelectric vibrator in which a vibrator drive electrode and a vibration pickup electrode are separated from each other.

For example, as shown in FIG. 10, the vibrator may be of a three-electrode structure such that one of two electrodes is split into a vibration pickup electrode 2901 and a vibrator drive electrode 2902.

Although, in this embodiment, the electrode of the piezoelectric vibrator of the energy confinement type also serves as a contact which is pressed against a subject and transmits vibrations to it, the electrode may be split into an electrode portion that causes the piezoelectric phenomenon and a contact portion that is pressed against the subject.

In that case, the same advantages as in the case of this embodiment will be obtained by using the size of the piezoelectric vibrator as the condition for describing an electric field used in deriving a Maison's equivalent circuit and using the size of the contact as the condition for describing the size of the vibrating portion used in deriving the Oeastreicher's theoretical expression.

Figure 15:
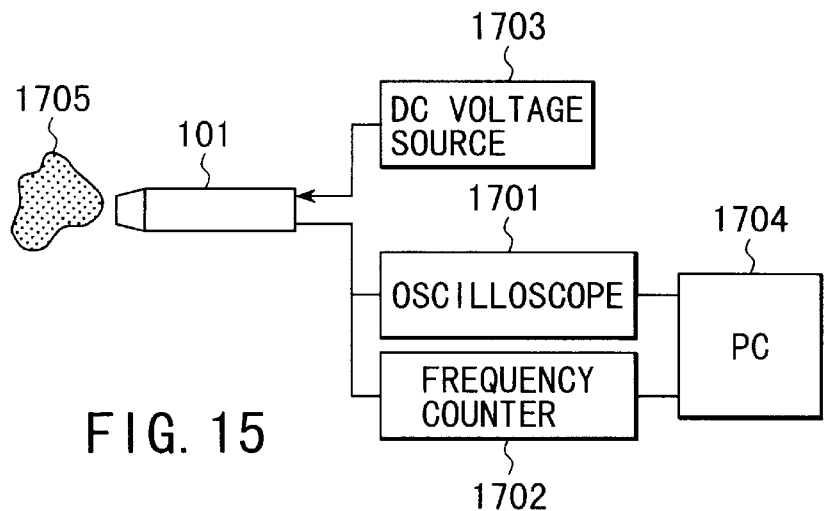
FIG. 15 shows a specific configuration of the tactile sensor signal processing devices according to the first and third embodiments of the present invention.

FIG. 15 shows a specific example of a tactile sensor signal processing device according to the first embodiment of the present invention.

This tactile sensor signal processing device is constructed from a tactile sensor 101 which detects the viscoelastic characteristics of a subject using changes in impedance characteristics of a piezoelectric vibrator 201 (see FIG. 16), a high-frequency oscilloscope 1701 which detects a change in the resonant resistance of the impedance characteristics, a frequency counter 1702 which detects a change in resonant frequency, a direct-current power supply 1703 for supplying a voltage to the piezoelectric vibrator 201, and a personal computer (PC) 1704 which controls the oscilloscope and the frequency counter, takes in output data from them, and computes independently each of the real part and the imaginary part of the shear viscoelastic coefficient indicating the viscoelastic characteristics of the subject on the basis of the results of detection by the oscilloscope and frequency counter and the prestored physical constants of the piezoelectric vibrator.

In the tactile sensor 101, the piezoelectric vibrator 201 is made of PZT and polarized in the direction of thickness.

The piezoelectric vibrator 201, 1.5 mm×1.5 mm and 120 $\mu$m in thickness, are formed through sputtering with Au electrodes of 6 mm in diameter at the centers of its surfaces in the direction of thickness, resulting in a structure of energy confinement in the thickness longitudinal mode.

The resonant frequency and the resonant resistance of the piezoelectric vibrator 201 are about 18 MHz and about 20 $\Omega$, respectively.

Figure 16:
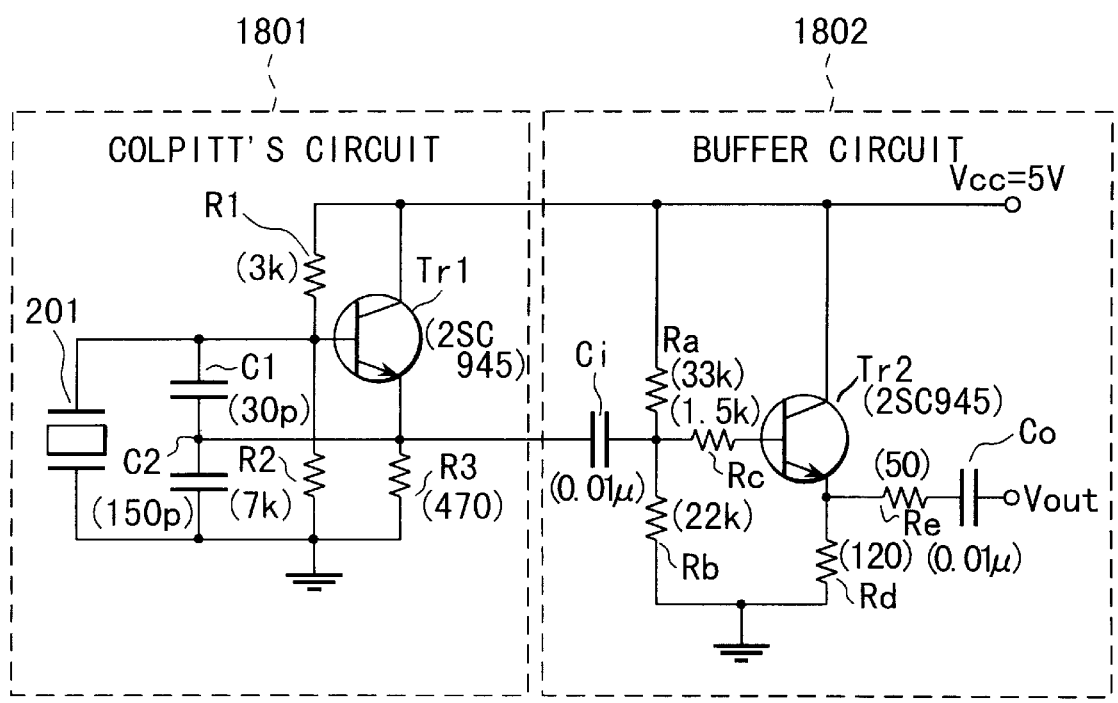
FIG. 16 shows a Colpitt's oscillator circuit connected to the piezoelectric vibrator and a buffer circuit connected to the Colpitt's oscillator circuit.

FIG. 16 shows a Colpitt's oscillator circuit 1801 connected to the piezoelectric vibrator 201 and a buffer circuit 1802 connected to the oscillator circuit 1801.

The Colpitt's oscillator circuit 1801 comprises a capacitor $C_1$ (30 pF), a capacitor $C_2$ (150 pF), a resistor $R_e$ (470 $\Omega$), a resistor $R_1$ (3 k$\Omega$), a resistor $R_2$ (7 k$\Omega$), a voltage terminal Vcc, and a transistor $Tr_1$ (2SC945).

The buffer circuit 1802 comprises a capacitor $C_i$ (0.01 $\mu$F), a capacitor $C_o$ (0.01 $\mu$F), a resistor $R_a$ (33 k$\Omega$), a resistor $R_b$ (22 k$\Omega$), a resistor $R_c$ (1.5 k$\Omega$), a resistor $R_d$ (120 $\Omega$), a resistor $R_e$ (50 $\Omega$), a voltage terminal Vcc, a transistor $Tr_2$ (2SC945), and an output terminal Vout.

In this Colpitt's oscillator 1801, when a DC voltage of 5V is supplied from the direct-current power supply 1703 through the voltage terminal Vcc to the piezoelectric vibrator 201 of energy confinement type, vibrations occur only in the electrode portion of the vibrator with a frequency of about 18 MHz and an amplitude of about 1.1V.

When the piezoelectric vibrator is brought into contact with a viscoelastic medium 1705 (see FIG. 15), the vibration frequency of the piezoelectric vibrator increases and the amplitude decreases according to the viscoelastic characteristics of the viscoelastic medium.

An increase in the vibration frequency ($\Delta F$) corresponds to a change in the resonance frequency of the piezoelectric vibrator 201 and a decrease in the amplitude ($\Delta A$) corresponds to a change in the resonance resistance.

These relationships can be found by measuring a resonant frequency change df, an impedance change dZ, a vibration frequency change $\Delta A$, and an amplitude change $\Delta A$ for two or more viscoelastic mediums and performing the method of least squares on the measurements.

In this manner, df and dZ were determined as $$df = 9.6 \times 10^{16} - 2.8 \times 10^6 \times \Delta F^2 \tag{56}$$

$$dZ = -378752 \Delta A - 893982 \tag{57}$$

The constants depend on the piezoelectric characteristics of the vibrator.

When a fixed piezoelectric vibrator is used with the tactile sensor 101, the coupling constant k, the elastic constant e, the size of the vibrating portion a, the resonant frequency $f_r$, and the angular frequency w are always held constant.

The density of a general viscoelastic medium can be assumed to be in the order of 1 g/cm$^3$.

The shear viscoelastic characteristics $\mu_1$ and $\mu_2$ and the real part E' and the imaginary part E" of the longitudinal complex elastic modulus are related by $$E'=\mu_1 \tag{58}$$

$$E''=\omega\mu_2 \tag{59}$$

By incorporating a signal processing program prepared using those relationships into the personal computer 1704 of FIG. 15, the viscoelastic characteristics (the real part E' and the imaginary part E") can be computed from changes in frequency and amplitude fed into the computer.

Figure 20:
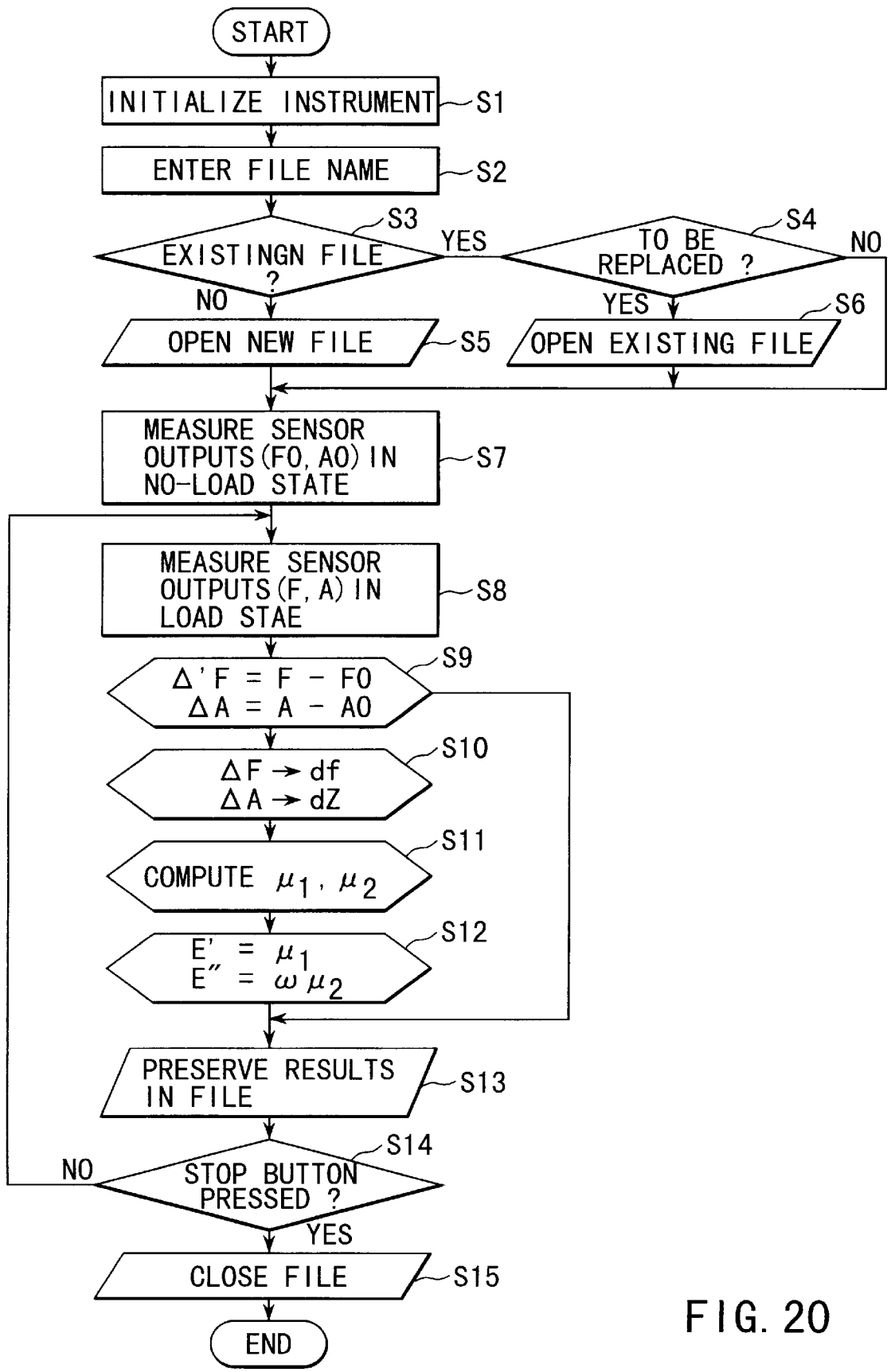
FIG. 20 is a flowchart illustrating the control and procedure associated with measurement of viscoelastic characteristics by the tactile sensor signal processing device according to the first embodiment of the present invention.

FIG. 20 is a flowchart for the control and procedure associated with measurement of the viscoelastic characteristics of the subject.

At the start of measurement, the measurement instrument is initialized (step S1) and then a file name is keyed in (step S2).

A decision is made as to whether the file is an existing one or not (step S3). If the file is an existing file, then a decision is made as to whether it is to be replaced or not (step S4).

If the file is not an existing file, then a new file is opened (step S5). If, on the other hand, an existing file is to be replaced, then it is opened (step S6).

Next, measurement of tactile sensor outputs ($F_0$, $A_0$) in the no-load state is carried out (step S7). After that, sensor outputs (F, A) in the load state when a viscoelastic medium is brought into contact with the sensor are measured (step S8).

On the basis of the measurements of the sensor outputs (F, A), computations of $\Delta F=F-F_0$ and $\Delta A=A-A_0$ (step S9), setting of $\Delta F \rightarrow df$ and $\Delta A \rightarrow dZ$ (step S10), computations of $\mu_1$ and $\mu_2$ (step S11) and computations of $E'=\mu_1$ and $E''=\mu_2$ (step S12) are carried out in sequence and the results are then preserved in the file (step S13).

A decision is made here as to whether a measurement stopping button has been pressed or not (step S14). When that button has been pressed, the file is closed (step S15) and the procedure comes to an end.

If, on the other hand, the button has not been pressed, then the flow returns to step S9 and the procedure is repeated.

In this example, a change in oscillation frequency and a change in amplitude are measured with the tactile sensor 101 brought into contact with a certain viscoelastic sample under a load and the real part E' and the imaginary part E" of the longitudinal complex elastic modulus are then computed from the measurements.

Figure 21A:
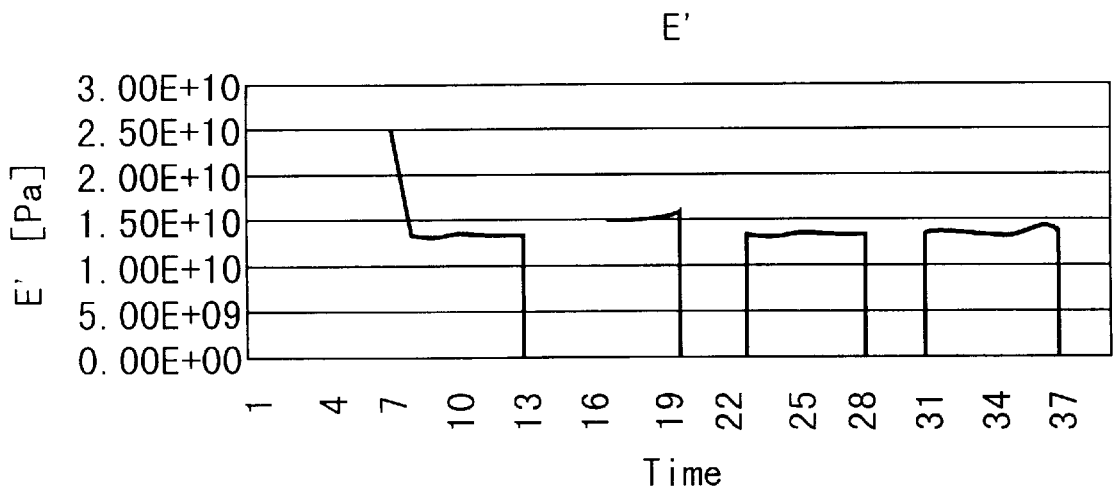
FIGS. 21A and 21B show real-time measurements in accordance with the procedure shown in FIG. 20.
Figure 21B:
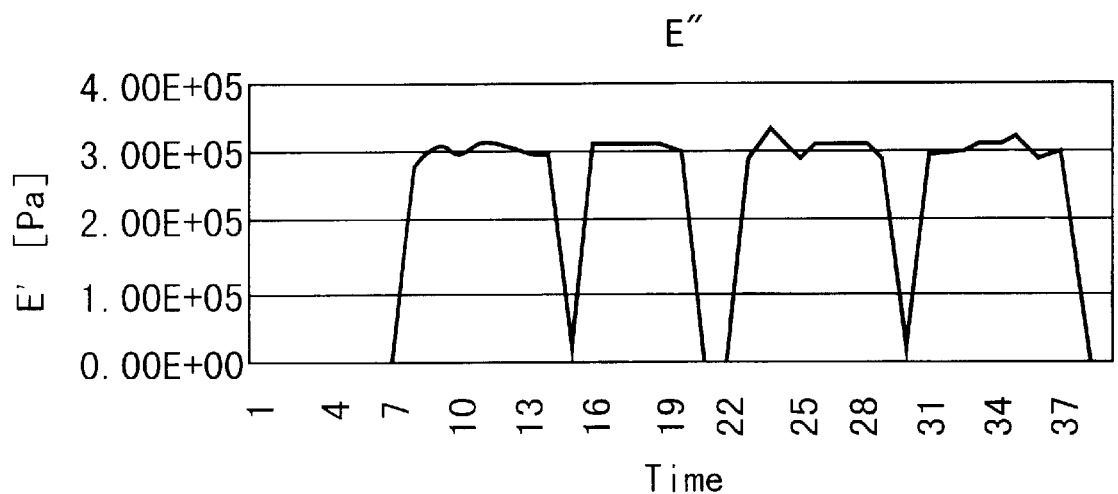

FIGS. 21A and 21B show the real-time measurements of the real part E' and the imaginary part E" of the longitudinal complex elastic modulus in the above manner.

As can be seen from those measurements, this specific example allows viscoelasticity measurement with good reproducibility to be made in real time.

It is known that living tissues exhibit the viscoelasticity as a result of muscles and intertissue fluids being intermingled, and morbid regions, such as tumors, indurations, etc., show different values for both the real part and the imaginary part of the viscoelastic modulus from those in normal regions. The tactile sensor signal processing device of this embodiment allows qualitative measurement of the viscoelastic characteristics of living tissues.

Second Embodiment

A second embodiment of the present invention will be described next with reference to FIG. 11.

The first embodiment is directed to a signal processing device adapted only for the piezoelectric phenomenon in the thickness longitudinal mode; thus, when the piezoelectric vibrator 201 of the tactile sensor 101 is replaced with one that utilizes another type of piezoelectric phenomenon, the signal processing device has to be reconfigured to adapt itself to that piezoelectric phenomenon.

In view of this drawback of the first embodiment, the second embodiment is thus intended to implement a tactile sensor signal processing device which allows the piezoelectric vibrator 201 to be removed and allows two or more types of piezoelectric vibrators to be used selectively.

Figure 11:
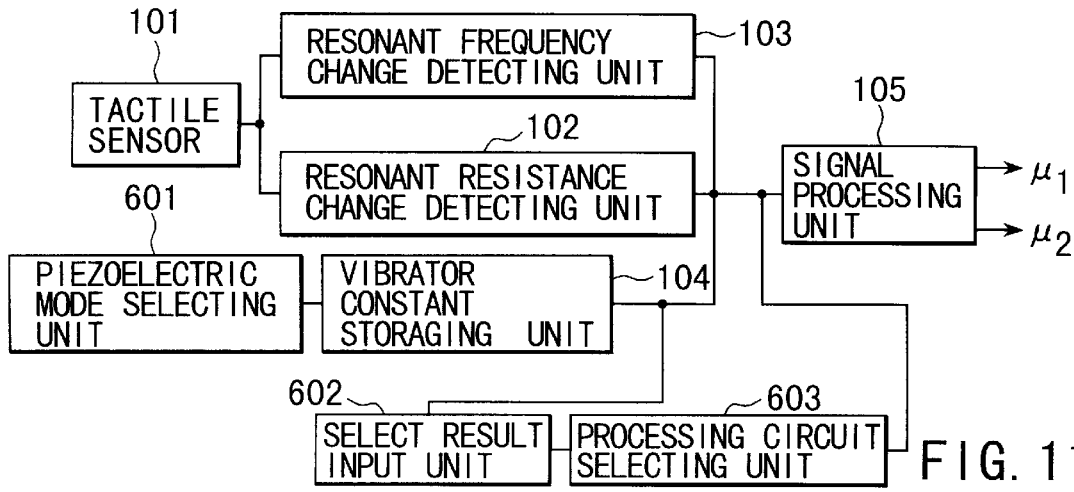
FIG. 11 is a block diagram of a tactile sensor signal processing device according to a second embodiment of the present invention.

FIG. 11 is a block diagram of a tactile sensor signal processing device 12 according to the second embodiment of the present invention.

As in the first embodiment, the tactile sensor signal processing device 12 includes a tactile sensor 101 which detects the viscoelastic characteristics of a subject under examination using changes in impedance characteristics of a piezoelectric vibrator, a resonant resistance change detecting unit 102 which detects a change in resonant resistance of the impedance characteristics of the piezoelectric vibrator, a resonant frequency change detecting unit 103 which detects a change in resonant frequency of the impedance characteristics of the piezoelectric vibrator, a vibrator constant storaging unit 104 in which physical constants of the piezoelectric vibrator are stored in advance, and a signal processing unit 105 which is responsive to the physical constants prestored in the storaging unit 104 and the results of detection by the resonant resistance change detecting unit 102 and the resonant frequency change detecting unit 103 to compute independently each of the real part and the imaginary part of the shear viscoelastic modulus as the viscoelastic characteristics of the subject.

In the vibrator constant storaging unit 104 are stored in advance piezoelectric constants for piezoelectric phenomena in the thickness longitudinal mode, the thickness transverse mode, and so on, coupling constants, the size of the vibrating portion of each of piezoelectric vibrators, and the density of each of the piezoelectric vibrators.

The vibrator constant storaging unit 104 is preceded by a piezoelectric phenomenon selecting unit 601 which makes a selection from types of piezoelectric phenomena determined by the direction of vibration and the direction of excitation electric fields, the result of selection being entered into the vibrator constant storaging unit 104.

The vibrator constant storaging unit 104 is followed by a selection result input unit 602 which selects the piezoelectric and coupling constants corresponding to the selected piezoelectric phenomenon from the vibrator constant storage unit, and a signal processing circuit selecting unit 603 which is responsive to vibrator constants from the selection result input unit 602 to select a signal processing circuit adapted for the selected piezoelectric phenomenon.

The circuit arrangements of the tactile sensor 101, the resonant resistance change detecting unit 102 and the resonant resistance change detecting unit 103 may be identical to those shown in FIG. 2A.

Figure 12:
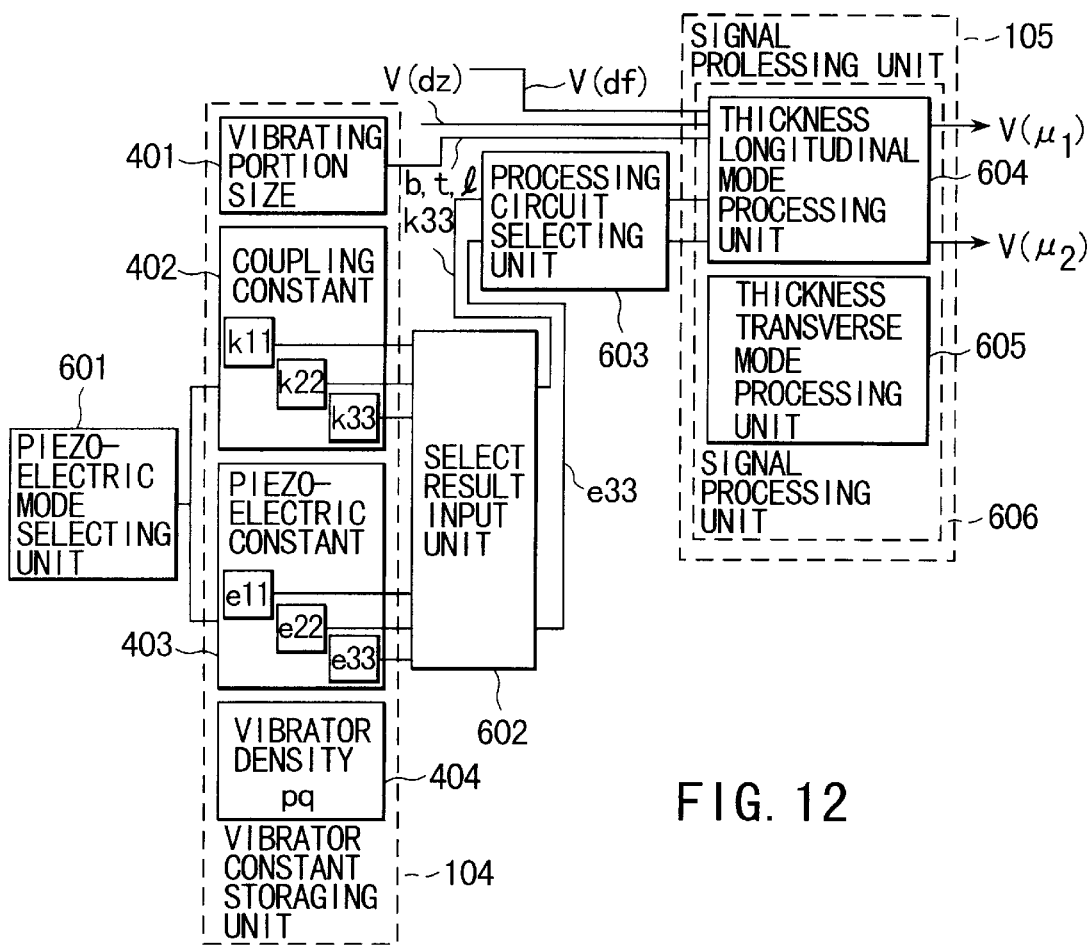
FIG. 12 shows the vibrator constant storage unit and a signal processing circuit contained in the signal processing unit of FIG. 11.

FIG. 12 shows details of the vibrator constant storage unit 104 and a signal processing circuit 606 built in the signal processing unit 105.

The signal processing circuit 606 comprises a thickness longitudinal mode processing circuit 604 and a thickness transverse mode (thickness slip mode) processing circuit 605.

In the above arrangement, the piezoelectric phenomenon selecting unit 601 selects the type of piezoelectric phenomenon associated with the piezoelectric vibrator 201 attached to the tactile sensor 101 as shown in FIG. 2. The selection result input unit 602 is responsive to the selecting unit 601 to take in constants corresponding to the piezoelectric phenomenon from the piezoelectric constants and the coupling constants in the vibrator constant storaging unit 104. In accordance with the vibrator constants taken in by the selecting unit 602, a signal processing circuit is selected which is adapted for the selected piezoelectric phenomenon, thus allowing the computation of the real part $\mu_1$ and the imaginary part $\mu_2$ of the shear elastic modulus.

The second embodiment allows viscoelastic characteristics to be detected accurately for each of piezoelectric phenomena because the viscoelastic characteristics detected by the tactile sensor 101 differ with the piezoelectric phenomena.

The piezoelectric phenomenon select unit 601 may be arranged not only to select vibrator constants corresponding to the piezoelectric phenomenon of the piezoelectric vibrator 201 but also to select a signal processing circuit corresponding to the piezoelectric phenomenon. As a result, even in the case where a piezoelectric vibrator of a different type of piezoelectric phenomenon is attached, the same tactile sensor signal processing device can be used to compute each of the real part $\mu_1$ and the imaginary part $\mu_2$ of the shear elastic modulus independently.

Third Embodiment

Next, a third embodiment of the present invention will be described.

The first embodiment uses the signal processing circuit based on the expressions derived for the thickness longitudinal mode. In this case, very many coefficients are involved in computations and the circuit becomes complex. Although the viscoelastic characteristics can be detected accurately, the computations tend to be time-consuming.

Thus, the third embodiment is intended to provide a simplified signal processing circuit that, using a viscoelastic medium for which the shear elastic modulus is known, measures a relationship between the shear elastic modulus and a change in impedance or frequency and then determines each of coefficients in the viscoelastic characteristic computation expression on the basis of the measurements.

Figure 13:
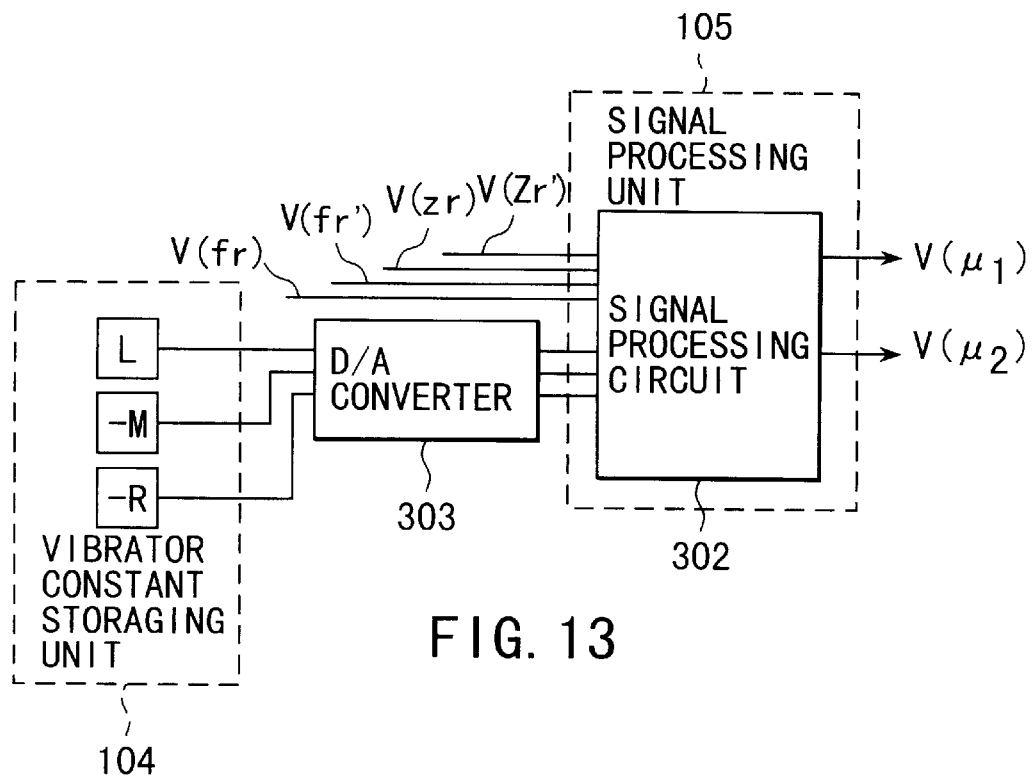
FIG. 13 shows the vibrator constant storage unit, the D/A converter, the signal processing unit, and a signal processing circuit in a third embodiment of the present invention.

FIG. 13 shows the vibrator constant storage unit 104 which is characteristic of the third embodiment, the D/A converter 303, the signal processing unit 105, and the signal processing circuit 302. In this figure, other corresponding components to those in the first embodiments are omitted.

In the vibrator constant storaging unit 104 are stored constants L, M, P and R which are determined in advance by measuring a relationship between the shear elastic modulus and a change in impedance or frequency through the use of a viscoelastic medium the shear elastic modulus of which is known and using the measurements.

When a fixed piezoelectric vibrator is used with the tactile sensor 101, the coupling constant k, the piezoelectric constant e, the dimensions a and l a of the vibrating portion of the vibrator, the resonant frequency $f_r$, and the angular frequency ω are always fixed.

Assuming the density of a general viscoelastic medium to be of the order of 1 g/cm³, the real part $\mu_1$ and the imaginary part $\mu_2$ of the shear elastic modulus derived in the first embodiment can be approximated as follows:

$$\mu_1 \rightarrow L(df+M'+N\sqrt{\mu_2}) \quad (60)$$

$$\mu_2 \rightarrow PdZ+R \quad (61)$$

In general, since $$\mu_1 >> \sqrt{\mu_2} \quad (62)$$

the above expressions are further rewritten as $$\mu_1 \rightarrow L*df+M \quad (63)$$

$$\mu_2 \rightarrow P*dZ+R \quad (64)$$

where L, M, M', N, P, and R are constants.

Of these constants, L, M, P and R are determined in advance by measuring a relationship between the shear elastic modulus and a change in impedance or frequency using a viscoelastic medium the shear elastic modulus of which is known and applying the method of least squares to the measurements.

In FIG. 13, a set of resonant frequency $f_r'$ from the resonant frequency change detect unit 102 and resonant resistance $Z_r'$ from the resonant resistance change detecting unit 103 is fed at the same time into the signal processing unit 105 which is the same as that shown in FIG. 3 via the gate 301 and resonant frequency and resonant resistance signals $V(f_r')$ and $V(Z_r')$ are entered into the signal processing circuit 302.

On the other hand, the resonant frequency $f_r$ and the resonant resistance $Z_r$ to which reference is made, which have been stored in the initial resonant frequency holding unit 304 and the initial resonant resistance holding unit 305 prior to the measurement, are entered into the signal processing circuit 302 as $V(f_r)$ and $V(Z_r)$.

The constants L, M, and R, which are constants determined in advance by measuring a relationship between the shear elastic modulus and a change in impedance or frequency using a viscoelastic medium the shear elastic modulus of which is known and applying the method of least squares to the measurements, have been stored in the vibrator constant storaging unit 104.

Note that M and R are entered as minus values.

These values are converted by the D/A converter 303 from digital signals into analog DC voltage signals V(L), V(–M) and V(–R) and then entered into the signal processing circuit 302.

Figure 14:
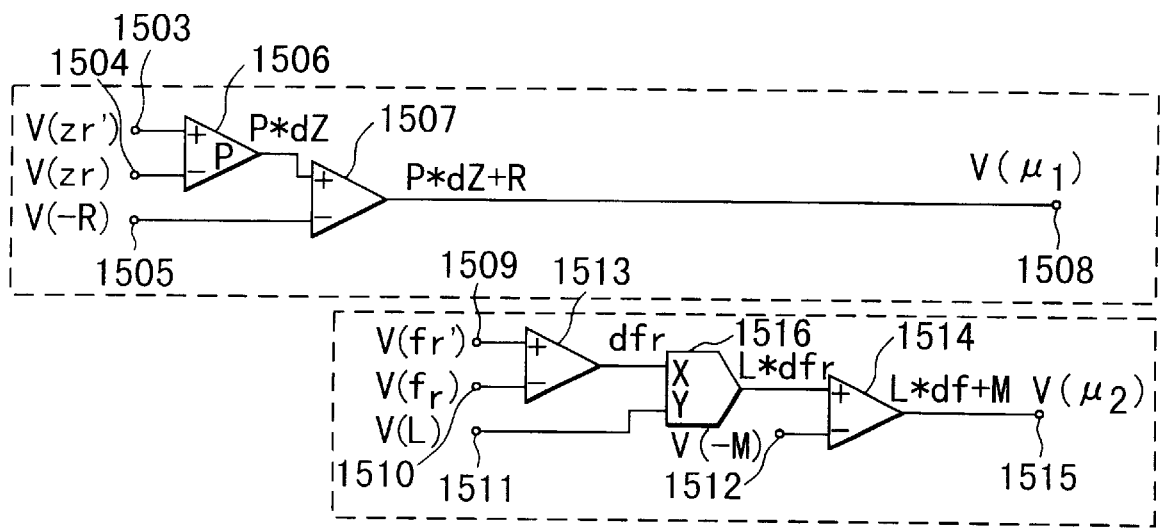
FIG. 14 shows an example of the signal processing circuit of the third embodiment.

FIG. 14 shows an example of the signal processing circuit 302 based on the above relational expressions.

The signal processing circuit is composed of computation circuits 1501 and 1502 for computing the real part $\mu_1$ and the imaginary part $\mu_2$ of the shear elastic modulus, respectively.

The constant P, determined in advance by measuring a relationship between the shear elastic modulus and a change in impedance or frequency using a viscoelastic medium the shear elastic modulus of which is known and applying the method of least squares to the measurements, is used as the amplification factor of a differential amplifier 1506 in the shear elastic modulus real part computation circuit 1502.

Hereinafter, the flow of signals in FIG. 14 will be described.

First, in the shear elastic modulus imaginary part computation circuit 1502, the direct-current signals $V(Z_r)$ and $V(Z_r')$ from input terminals 1503 and 1504 are converted through the differential amplifier 1506 having an amplification factor of P into a direct-current voltage signal V(P*dZ).

The direct-current voltage signal V(P*dZ) and a direct-current voltage signal V(–R) from input terminal 1505 are applied to a differential amplifier 1507 with an amplification factor of unity, yielding a direct-current voltage signal V(P*dZ+R).

This result is obtained from an output terminal 1508 as V($\mu_2$).

On the other hand, in the shear elastic modulus real part computation circuit 1501, the direct-current signals V(f$_r$') and V(f$_r$) from input terminals 1509 and 1510 are converted through a differential amplifier 1513 having an amplification factor of unity into a direct-current voltage signal v(df$_r$).

The direct-current voltage signal V(df$_r$) and a direct-current voltage signal V(L) from input terminal 1511 are applied to a multiplier 1516 to produce a direct-current voltage signal V(L*df$_r$).

The direct-current voltage signal V(L*df$_r$) and a direct-current voltage signal V(−M) from input terminal 1512 are applied to a differential amplifier 1514 with an amplification factor of unity, yielding a direct-current voltage signal V(−L*df$_r$+M).

This result is obtained from an output terminal 1515 as V($\mu_1$).

The third embodiment thus arranged can make the signal processing circuit very simple in construction and can perform fast computations by measuring a relationship between the shear elastic modulus and a change in impedance or frequency using a viscoelastic medium the shear elastic modulus of which is known and determining the coefficients involved in the expressions for computing viscoelastic characteristics on the basis of the measurements.

FIG. 15 shows a specific example of a tactile sensor signal processing device according to the third embodiment of the present invention.

This tactile sensor signal processing device is constructed from a tactile sensor 101 which detects the viscoelastic characteristics of a subject using changes in impedance characteristics of a piezoelectric vibrator 201 (see FIG. 16), a high-frequency oscilloscope 1701 which detects a change in the resonant resistance of the impedance characteristics, a frequency counter 1702 which detects a change in resonant frequency, a direct-current power supply 1703 for supplying a voltage to the piezoelectric vibrator 201, and a personal computer (PC) 1704 which controls the oscilloscope and the frequency counter, takes in output data from them, and computes independently each of the real part and the imaginary part of the shear viscoelastic coefficient indicating the viscoelastic characteristics of the subject on the basis of the results of detection by the oscilloscope and frequency counter and the prestored physical constants of the piezoelectric vibrator.

In the tactile sensor 101, the piezoelectric vibrator 201 is made of PZT and polarized in the direction of thickness.

The piezoelectric vibrator 201, 1.5 mm×1.5 mm and 120 $\mu$m in thickness, are formed through sputtering with Au electrodes of 6 mm in diameter at the centers of its surfaces in the direction of thickness, resulting in a structure of energy confinement in the thickness longitudinal mode.

The resonant frequency and the resonant resistance of the piezoelectric vibrator 201 are about 18 MHz and about 20 Ω, respectively.

FIG. 16 shows a Colpitt's oscillator circuit 1801 connected to the piezoelectric vibrator 201 and a buffer circuit 1802 connected to the oscillator circuit 1801.

The Colpitt's oscillator circuit 1801 comprises a capacitor C$_1$ (30 pF), a capacitor C$_2$ (150 pF), a resistor R$_3$ (470 Ω), a resistor R$_1$ (3 kΩ), a resistor R$_2$ (7 kΩ), a voltage terminal Vcc, and a transistor Tr$_1$ (2SC945).

The buffer circuit 1802 comprises a capacitor C$_i$ (0.01 $\mu$F), a capacitor C$_o$ (0.01 $\mu$F), a resistor R$_a$ (33 kΩ), a resistor R$_b$ (22 kΩ), a resistor R$_c$ (1.5 kΩ), a resistor R$_d$ (120 Ω), a resistor R$_e$ (50 Ω), a voltage terminal Vcc, a transistor Tr$_2$ (2SC945), and an output terminal Vout.

In this Colpitt's oscillator 1801, when a DC voltage of 5V is supplied from the direct-current power supply 1703 through the voltage terminal Vcc to the piezoelectric vibrator 201 of energy confinement type, vibrations occur only in the electrode portion of the vibrator with a frequency of about 18 MHz and an amplitude of about 1.1V.

When the piezoelectric vibrator is brought into contact with a viscoelastic medium 1705, the vibration frequency of the piezoelectric vibrator increases and the amplitude decreases according to the viscoelastic characteristics of the viscoelastic medium.

An increase in the vibration frequency corresponds to a change in the resonance frequency of the piezoelectric vibrator 201 and a decrease in the amplitude corresponds to a change in the resonance resistance.

When a fixed piezoelectric vibrator is used with the tactile sensor 101, the coupling constant k, the piezoelectric constant e, the dimensions a and l of the vibrating portion of the vibrator, the resonant frequency f$_r$, and the angular frequency ω are always fixed.

Assuming the density of a general viscoelastic medium to be of the order of 1 g/cm$^3$, the real part E' and the imaginary part E" of the viscoelastic coefficient can be approximated as follows:

$$E' \rightarrow Ldf + M \tag{65}$$

$$E'' \rightarrow PdZ + R \tag{66}$$

where L, M, P and R are constants.

These constants are determined in advance by measuring a relationship between the shear elastic modulus and a change in impedance or frequency using a viscoelastic medium the shear elastic modulus of which is known and applying the method of least squares to the measurements.

In reality, measurement of the acoustic impedances of viscoelastic mediums through the use of a nominal 10-MHz ultrasound probe and computation of the viscoelastic modulus (the real part E' and the imaginary part E") from the measurements resulted in Table 1.

TABLE 1

| Sample | E'(Pa) | E"(Pa) |
| --- | --- | --- |
| HC00V | 1.88 × 10$^9$ | 1.29 × 10$^6$ |
| Hc04V | 1.86 × 10$^9$ | 5.90 × 10$^5$ |
| MC04 | 1.62 × 10$^9$ | 3.60 × 10$^5$ |
| α | 9.70 × 10$^8$ | 2.10 × 10$^5$ |
| θ | 1.08 × 10$^9$ | 3.50 × 10$^5$ |

Figure 17:
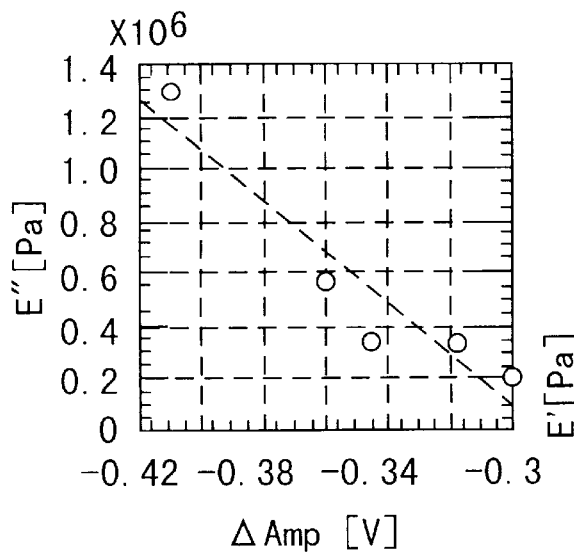
FIG. 17 shows viscoelastic modulus imaginary part E" versus amplitude change ΔAmp.

Measurement of changes in vibration frequency and changes in amplitude for viscoelastic mediums whose viscoelastic characteristics are known as shown in TABLE 1 with the tactile sensor 101 brought into contact with them shows that there is such a relationship as shown in FIG. 17 between the amplitude change ΔAmp and the imaginary part E" of the viscoelastic modulus. The relational expression is given by $$E'' = -9.7e + 6\Delta Amp - 2.8e + 6 \tag{67}$$

Here, the unit is V for ΔAmp and Pa for E".

Figure 18:
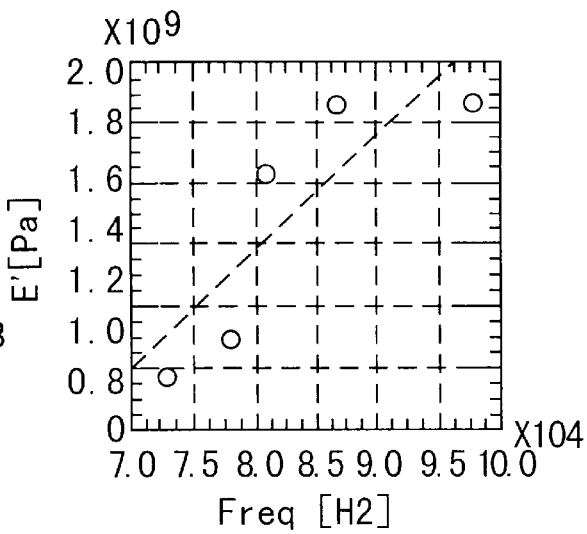
FIG. 18 shows viscoelastic modulus real part E' versus frequency change ΔFreq.
Figure 19:
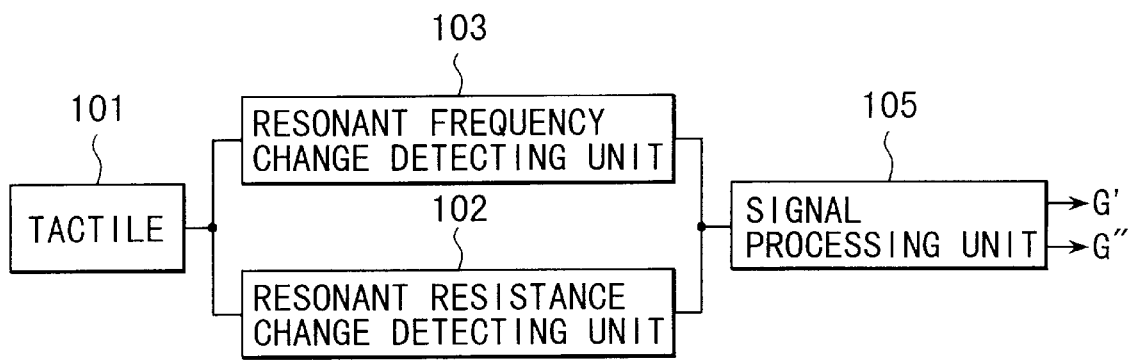
FIG. 19 is a schematic representation of a conventional tactile sensor signal processing device.

On the other hand, there is such a relationship as shown in FIG. 18 between the frequency change ΔFreq and the real part E' of the viscoelastic modulus and the relational expression is given by $$E' = 39444\Delta Freq - 1.8e + 9 \tag{68}$$

Here, the unit is Hz for ΔAmp and Pa for E'.

By incorporating into the personal computer (PC) 1704 a signal processing program prepared using the relational expressions thus obtained, the viscoelastic characteristics (the real part E' and the imaginary part E") of a subject of measurement by the tactile sensor 101 can be computed from detected frequency and amplitude changes.

Next, actual observations of viscoelastic characteristics of silicone gel (TSE3032 by Toshiba Silicone Company) prepared on acrylic plate are illustrated.

In this case, two samples of 0.5 mm and 10 mm in thickness were prepared on acrylic plates.

For the two samples, the observations of the frequency and amplitude changes and the computational results of the moduli of viscoelasticity (E', E") in accordance with the above expressions are shown in Table 2.

TABLE 2

| | ΔFreq[kHz] | ΔAmp[V] | E'[Pa] | E"[Pa] |
|---|---|---|---|---|
| Thickness 0.5 mm | 97 | −0.29 | $2.0 \times 10^9$ | $1.3 \times 10^4$ |
| Thickness 10 mm | 87.5 | −0.3 | $1.3 \times 10^9$ | $11 \times 10^4$ |

Table 2 shows that, for the silicone gel of 0.5 mm in thickness, the computed real part E' (elasticity) of viscoelastic characteristics is smaller than that for the silicone gel of 10 mm thick, while the imaginary part E" (viscosity) is larger than that for the silicone gel of 10 mm thick.

In this instance, it is probable that the tactile sensor detected not only the viscoelastic characteristics of the silicone gel of 0.5 mm thick but also those of the underlying acrylic plate because the gel is very thin.

Such outputs of the tactile sensor agree with the human tendency to feel as if silicone gel became hard when it is very thin and acrylic resin exists underneath.

It is known that living tissues exhibit the viscoelasticity as a result of muscles and intertissue fluids being intermingled, and morbid regions, such as tumors, indurations, etc., show different values for both the real part and the imaginary part of the viscoelastic modulus from those in normal regions. The tactile sensor signal processing device of this embodiment can detect the viscoelastic characteristics of living tissues to match the human sense.

The specification described so far contains the following inventions:

(1) A tactile sensor signal processing device for detecting the viscoelastic characteristics of a subject through changes in impedance characteristics of a vibrator, comprising:
  a tactile sensor using a piezoelectric vibrator;
  resonant resistance change detect means for detecting a change in resonant resistance of the impedance characteristics of the piezoelectric vibrator;
  resonant frequency change detect means for detecting a change in resonant frequency of the impedance characteristics of the piezoelectric vibrator;
  vibrator constant storage means for prestoring physical constants including the size of a vibrating portion of the piezoelectric vibrator, piezoelectric and coupling constants associated with a piezoelectric phenomenon of the piezoelectric vibrator, the density of the piezoelectric vibrator, and the size of a contact that is pressed against the subject for applying vibrations to it; and
  signal processing means responsive to the results of detection by the resonant resistance change detect means and the resonant frequency change detect means, and the physical constants stored in the vibrator constant storage means for independently computing real and imaginary parts of shear elastic modulus indicating the viscoelastic characteristics of the subject.

The invention (1) corresponds to the first, second, and third embodiments.

The resonant resistance change detect means and the resonant frequency change detect means, while corresponding to the oscillator circuit in those embodiments, may comprise an impedance measurement instrument.

Operation

The resonant resistance $Z_r$ detected by the resonant resistance change detect means and the resonant frequency $f_r$ detected by the resonant frequency detect means are fed into the signal processing means together with the size of the vibrating portion of the piezoelectric vibrator, the piezoelectric and coupling constants associated with the piezoelectric mode of the piezoelectric vibrator used, the density of the piezoelectric vibrator, and the size of the contact, which have been stored in advance in the vibrator constant storage means. The signal processing means, into which a computation procedure has been incorporated, computes the real part $\mu_1$ and the imaginary part $\mu_2$ of shear elastic modulus indicating the viscoelastic characteristics of the subject.

Advantages

The signal processing means allows the real part $\mu_1$ and the imaginary part $\mu_2$ of shear elastic modulus based on the piezoelectric phenomenon of the piezoelectric vibrator to be computed.

The impedance (resonant resistance) dZ and the resonant frequency change df are associated with the real part $\mu_1$ and the imaginary part $\mu_2$ of shear elastic modulus, respectively. Their relationship can be derived on the basis of the piezoelectric phenomenon determined by the vibration direction of the piezoelectric vibrator and the direction of the excitation electric field.

If the density of the piezoelectric vibrator, the dimensions of the oscillating portion, the piezoelectric constant, the coupling constant, and the resonant frequency $f_r$ and resistance $Z_r$ at no-load time are already known, it is not until both the resonant frequency change and the resonant resistance change are measured that the real part $\mu_1$ and the imaginary part $\mu_2$ of shear elastic modulus can be computed to detect the viscoelastic characteristics.

The living tissues exhibit the viscoelastic characteristics as the result of muscles and intertissue fluids being interwined with one another. In morbid regions such as tumors and indurations, both the real part $\mu_1$ and the imaginary part $\mu_2$ of the shear viscoelastic coefficient $\mu$ change. More detailed biological information can be obtained by detecting the viscoelastic characteristics separately using the piezoelectric phenomenon of the piezoelectric vibrator as in this invention (2) The tactile sensor signal processing device according to (1), wherein the signal processing means comprises: a signal processing circuit responsive to the results of detection by the resonant resistance change detect means and the resonant frequency change detect means, and the physical constants stored in the vibrator constant storage means for computing the real and imaginary parts of the shear elastic modulus of the subject through the use of computational expressions for computing each of the real and imaginary parts of the shear elastic modulus independently; input means for allowing the results of detection by the resonant resistance change detect means and the resonant frequency change detect means to be entered into the signal processing circuit at the same time; and output means for outputting the results of computation by the signal processing circuit.

Invention (2) corresponds to the first, second, and third embodiments.

The input means in invention (2) corresponds to the gates in the embodiments.

Operation

The resonant resistance change and the resonant frequency change are fed through the input means into the signal processing circuit at the same time. Using the computational expressions, the signal processing circuit computes each of the real and imaginary parts of the shear elastic modulus independently.

Advantages

Each of the real and imaginary parts of the shear elastic modulus can be computed independently in real time.

(3) The tactile sensor signal processing device according to (2), wherein the signal processing circuit comprises a processing circuit corresponding to the piezoelectric phenomenon of the piezoelectric vibrator and, in response to inputting the physical constants associated with the piezoelectric phenomenon of the piezoelectric vibrator from the vibrator constant storage means to the processing circuit, performs computational processing through the use of the computational expressions for computing each of the real and imaginary parts of the shear elastic modulus independently.

Invention (3) corresponds to the first and second embodiments.

The piezoelectric phenomenon in invention (3) is the thickness longitudinal mode, thickness transverse mode, or the like and refers to types of a vibration direction of the piezoelectric vibrator and an electric field applied thereto.

Operation

The piezoelectric phenomenon select means inputs a set of physical constants stored in the vibrator constant storage means to the signal processing circuit according to the type of the piezoelectric phenomenon of the piezoelectric vibrator used, so that the signal processing circuit computes the real part $\mu_1$ and the imaginary part $\mu_2$ of shear elastic modulus.

Advantages

The viscoelastic characteristics detected by the tactile sensor vary with the piezoelectric phenomena. Thus, accurate viscoelastic characteristics can be detected according to the piezoelectric phenomenon involved.

(4) The tactile sensor signal processing device according to (3), wherein, when the piezoelectric phenomenon is the thickness longitudinal mode, the signal processing means is responsive to changes in resonant frequency and resonant resistance to compute each of the real part $\mu_1$ and the imaginary part $\mu_2$ of the shear elastic modulus independently in accordance with the following two expressions:

$$\mu_1 = \frac{\omega}{18a^2\pi^2 f_r}\{2a^4\pi^2\rho\omega^2 f_r + 9a^4 A^2\pi^2\rho^2\omega^2 f_r -$$
$$3a^3 A\pi^{3/2}\rho\omega^{3/2}\sqrt{9a^2 A^2\pi\rho^2\omega + 32dZ_{3e}le_{33}^2}f_r +$$
$$4df f^4 \rho_q \omega(k_{33} - 1)\}$$

$$\mu_2 = -\frac{1}{18\pi}\{-9a^2 A^2\pi\rho^2\omega - 16dZ_{3e}le_{33}^2 -$$
$$2aA\rho\sqrt{\pi\omega}\sqrt{9a^2 A^2\pi\rho^2\omega + 32dZ_{3e}le_{33}^2}$$

where
A=Cos [0.5 Tan$^{-1}$[$\omega$]]=Sin [0.5 Tan$^{-1}$[$\omega$]]
$\omega$=angular frequency
dZ=change in resonant resistance
df=change in resonant frequency
$f_r$=resonant frequency at no-load time
$\rho$=density of the viscoelastic medium
a=radius of the vibrating portion of the vibrator
l=thickness of the vibrator
$e_{33}$=piezoelectric constant of the piezoelectric vibrator
$k_{33}$=coupling constant of the piezoelectric vibrator, and
$\rho_q$=density of the piezoelectric vibrator.
This invention corresponds to the first embodiment.

Operation

The density $\rho_q$ of the piezoelectric vibrator, the dimensions a and l of the oscillating portion, the piezoelectric constant $e_{33}$, the coupling constant $k_{33}$, the resonant frequency $f_r$ at no-load time, the impedance (resonant resistance) change dZ and the resonant frequency change df are entered into the circuit prepared based on the computational expressions for obtaining the real part $\mu_1$ and the imaginary part $\mu_2$ of the shear elastic modulus, thereby computing the real part $\mu_1$ and the imaginary part $\mu_2$ of the shear elastic modulus.

Advantages

A signal processing circuit can be made to match the piezoelectric phenomenon in the thickness longitudinal mode and the real part $\mu_1$ and the imaginary part $\mu_2$ of the shear elastic modulus can be computed.

(5) The tactile sensor signal processing device according to (3), wherein the signal processing circuit comprises a plurality of processing circuits each corresponding to a respective one of different piezoelectric modes associated with a plurality of piezoelectric vibrators, each set of physical constants corresponding to a respective one of the piezoelectric modes being stored in the vibrator constant storage means, and wherein the tactile sensor signal processing device further comprises piezoelectric mode select means for allowing a selection from the piezoelectric modes associated with the plurality of piezoelectric vibrators from outside, processing circuit select means for selecting a processing circuit corresponding to a selected piezoelectric mode from the plurality of processing circuits, and vibrator constant select means for selecting a set of physical constants corresponding to the selected piezoelectric mode from the vibrator constant storage means.

This invention corresponds to the second embodiment.

Operation

The piezoelectric phenomenon select means selects the type of piezoelectric phenomenon of the piezoelectric vibrator. The selection result input unit 602 is responsive to the selecting unit 601 to take in constants corresponding to the piezoelectric phenomenon from the piezoelectric constants and the coupling constants in the vibrator constant storaging unit 104. In response to the vibrator constants taken in by the select means 602, a signal processing circuit is selected which is adapted for the selected piezoelectric phenomenon, thus computing the real part $\mu_1$ and the imaginary part $\mu_2$ of the shear elastic modulus.

Advantages

This invention allows viscoelastic characteristics to be detected accurately for each of piezoelectric phenomena because the viscoelastic characteristics detected by the tactile sensor differ with the piezoelectric phenomena.

In addition, the piezoelectric phenomenon select means may be arranged not only to select vibrator constants corresponding to the piezoelectric phenomenon of the piezoelectric vibrator 201 but also to select a signal processing circuit corresponding to the piezoelectric phenomenon. As a result, even in the case where a piezoelectric vibrator of a different type of piezoelectric phenomenon is attached, the same tactile sensor signal processing device can be used to compute each of the real part $\mu_1$ and the imaginary part $\mu_2$ of the shear elastic modulus independently.

(6) A tactile sensor signal processing device for detecting the viscoelastic characteristics of a subject through changes in impedance characteristics of a vibrator, comprising:

a tactile sensor using a piezoelectric vibrator;

resonant resistance change detect means for detecting a change in resonant resistance of the impedance characteristics of the piezoelectric vibrator;

resonant frequency change detect means for detecting a change in resonant frequency of the impedance characteristics of the piezoelectric vibrator;

vibrator constant storage means for prestoring constants involved in computation of shear elastic modulus indicating the viscoelastic characteristics of the subject; and signal processing means responsive to the results of detection by the resonant frequency change detect means and the resonant resistance change detect means and the constants stored in the constant storage means for computing independently each of the real part $\mu_1$ and the imaginary part $\mu_2$ of the shear elastic modulus of the subject on the basis of the following two expressions:

$$df = L + M \times \Delta F^N$$

where $\Delta F$ is the change in oscillating frequency, dZ is the change in resonant resistance, df is the change in resonant frequency, and L, M and N are constants, and $$dZ = R \times \Delta A + S$$

where $\Delta A$ is the change in amplitude, dZ is the change in resonant resistance, and R and S are constants.

This invention corresponds to the third embodiment.

Operation

A change in oscillation frequency in the Colpitt's oscillator circuit is converted into a resonant frequency change in the piezoelectric vibrator and an amplitude change is converted into a resonant resistance change. The resulting resonant frequency change and resonant frequency change are used in the above computational expressions to compute independently each of the real part $\mu_1$ and the imaginary part $\mu_2$ of the shear elastic modulus.

Advantages

The real part $\mu_1$ and the imaginary part $\mu_2$ of the shear elastic modulus can be computed quantitatively and in real time from the tactile sensor outputs.

(7) The tactile sensor signal processing device according to (6), wherein the constants are each derived from measurements of changes in resonant resistance and changes in resonant frequency of a plurality of viscoelastic samples the viscoelastic characteristics of which are known in advance.

This invention corresponds to the third embodiment.

Operation

The viscoelastic characteristics of a plurality of viscoelastic samples are measured by a viscoelasticity measurement instrument based on a method that differs from that of the present invention and some of them for which stable measurements are obtained are selected in advance. A frequency change and an amplitude change are measured by the tactile sensor for each of the selected samples. Functions are then determined through the use of the method of least squares, which relate the real part $\mu_1$ and the imaginary part $\mu_2$ of the shear elastic moduli of the selected samples which have been measured to frequency changes and amplitude changes, respectively, of the selected samples.

Advantages

The signal processing means is only required to be arranged to perform the functions that relate the real part $\mu_1$ and the imaginary part $\mu_2$ of shear elastic modulus to a frequency change and an amplitude change, respectively.

(8) The tactile sensor signal processing device according to (1) or (6), wherein the piezoelectric vibrator of the tactile sensor is formed in the shape of a semi-circle.

(9) The tactile sensor signal processing device according to (1) or (6), wherein the piezoelectric vibrator of the tactile sensor is formed in the shape of a ring.

(10) The tactile sensor signal processing device according to (1) or (6), wherein the piezoelectric vibrator of the tactile sensor is formed in the shape of a sphere.

(11) The tactile sensor signal processing device according to (1) or (6), wherein the piezoelectric vibrator of the tactile sensor is formed in the shape of a rectangular prism.

(12) The tactile sensor signal processing device according to (1) or (6), wherein the piezoelectric vibrator of the tactile sensor is formed in the shape of a drainpipe.

(13) The tactile sensor signal processing device according to (1) or (6), wherein the piezoelectric vibrator of the tactile sensor is formed in the shape of a cylinder.

(14) The tactile sensor signal processing device according to (1) or (6), wherein the piezoelectric vibrator of the tactile sensor is formed in the shape of a disk.

(15) The tactile sensor signal processing device according to (1) or (6), wherein the piezoelectric vibrator of the tactile sensor is of an energy confinement type.

(16) The tactile sensor signal processing device according to (1) or (6), wherein the piezoelectric vibrator of the tactile sensor has a three-terminal type of electrode structure.

(17) The tactile sensor signal processing device according to (1) or (6), wherein the piezoelectric vibrator of the tactile sensor has its one electrode doubled as a contact which is brought into contact with the subject.

As described above in detail, the present invention provides a tactile sensor signal processing device which eliminates the need of finding experimentally equipment coefficients required to detect viscoelastic characteristics provided that the displacement direction of a piezoelectric vibrator used, an electric field, mechanical terminal conditions and electrical conditions are obvious in advance and can obtain more detailed biological information in a short time through the use of those numerical values. That is, the present invention allows real-time measurement and hence requires shorter measurement time.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. A tactile sensor signal processing device for detecting viscoelastic characteristics of a subject, comprising:
   a tactile sensor that utilizes a piezoelectric vibrator;
   a resonant resistance change detecting unit that detects a change in resonant resistance of impedance characteristics of the piezoelectric vibrator;
   a resonant frequency change detecting unit that detects a change in resonant frequency of the impedance characteristics of the piezoelectric vibrator;
   a vibrator constant storage unit that prestores physical constants including a size of a vibrating portion of the piezoelectric vibrator, piezoelectric and coupling constants associated with a piezoelectric phenomenon of the piezoelectric vibrator, density of the piezoelectric vibrator, and a size of a contact that is pressed against the subject for applying vibrations to the subject; and
   a signal processing unit that, responsive to results of detection by the resonant resistance change detecting unit and the resonant frequency change detecting unit and the physical constants stored in the vibrator constants storage unit, independently computes real and imaginary parts of shear elastic modulus indicating the viscoelastic characteristics of the subject;
   wherein the signal processing unit comprises:
      a signal processing circuit, responsive to the results of detection by the resonant resistance change detecting unit and the resonant frequency change detecting unit, and the physical constants stored in the vibrator constant storage unit, for computing the real and imaginary parts of the shear elastic modulus of the subject using computational expressions for computing each of the real and imaginary parts of the shear elastic modulus independently;
      an input device through which the results of detection by the resonant resistance change detecting unit and the resonant frequency change detecting unit are entered into the signal processing circuit at the same time; and
      an output device that outputs results of computation by the signal processing circuit.

2. The tactile sensor signal processing device according to claim 1, wherein the signal processing circuit comprises a processing circuit corresponding to the piezoelectric phenomenon of the piezoelectric vibrator and, in response to an input of the physical constants associated with the piezoelectric phenomenon of the piezoelectric vibrator from the vibrator constant storage unit to the processing circuit, performs computational processing using the computational expressions for computing each of the real and imaginary parts of the shear elastic modulus independently.

3. The tactile sensor signal processing device according to claim 2, wherein, when the piezoelectric phenomenon is a thickness longitudinal mode, the signal processing unit is responsive to detected changes in the resonant frequency and the resonant resistance to compute each of the real part $\mu_1$ and the imaginary part $\mu_2$ of the shear elastic modulus independently in accordance with the following two expressions:

$$\mu_1 = \frac{\omega}{18a^2\pi^2 f_r}\{2a^4\pi^2\rho\omega^2 f_r + 9a^4 A^2\pi^2\rho^2\omega^2 f_r -$$
$$3a^3 A\pi^{3/2}\rho\omega^{3/2}\sqrt{9a^2 A^2\pi\rho^2\omega + 32dZ_{3e}le_{33}^2 f_r} +$$
$$4dfl^4\rho_q\omega(k_{33}-1)\}$$

$$\mu_2 = -\frac{1}{18\pi}\{-9a^2 A^2\pi\rho^2\omega - 16dZ_{3e}le_{33}^2 -$$
$$2aA\rho\sqrt{\pi\omega}\sqrt{9a^2 A^2\pi\rho^2\omega + 32dZ_{3e}le_{33}^2}$$

where
   $A = \text{Cos}[0.5\,\text{Tan}^{-1}[\omega]] = \text{Sin}[0.5\,\text{Tan}^{-1}[\omega]]$
   $\omega$ = angular frequency
   $dZ$ = change in resonant resistance
   $df$ = change in resonant frequency
   $f_r$ = resonant frequency at no-load time
   $\rho$ = density of the viscoelastic medium
   $a$ = radius of the vibrating portion of the vibrator
   $l$ = thickness of the vibrator
   $e_{33}$ = piezoelectric constant of the piezoelectric vibrator
   $k_{33}$ = coupling constant of the piezoelectric vibrator, and
   $\rho_q$ = density of the piezoelectric vibrator.

4. The tactile sensor signal processing device according to claim 2, wherein:
   the signal processing circuit comprises a plurality of processing circuits each corresponding to a respective one of different piezoelectric modes associated with a plurality of piezoelectric vibrators,
   the vibrator constant storage unit stores a plurality of sets of physical constants each corresponding to a respective one of the piezoelectric modes, and
   the tactile sensor signal processing device further comprises a piezoelectric mode selecting unit that allows a selection from among the piezoelectric modes associated with the plurality of piezoelectric vibrators from outside, a processing circuit selecting unit that selects a processing circuit corresponding to a selected piezoelectric mode from among the plurality of processing circuits, and a vibrator constant selecting unit that selects a set of physical constants corresponding to the selected piezoelectric mode from the vibrator constant storage unit.

5. A tactile sensor signal processing device for detecting viscoelastic characteristics of a subject, comprising:
   a tactile sensor that utilizes a piezoelectric vibrator;
   a resonant resistance change detecting unit that detects a change in resonant resistance of impedance characteristics of the piezoelectric vibrator;
   a resonant frequency change detecting unit that detects a change in resonant frequency of the impedance characteristics of the piezoelectric vibrator;
   a vibrator constant storage unit that prestores constants involved in computation of shear elastic modulus indicating the viscoelastic characteristics of the subject; and a signal processing unit that, responsive to results of detection by the resonant frequency change detecting unit and the resonant resistance change detecting unit and the constants stored in the vibrator constant storage unit, independently computes each of a real part $\mu_1$ and an imaginary part $\mu_2$ of the shear elastic modulus of the subject based on the following two expressions:

$$df = L + M \times \Delta F^N$$

where $\Delta F$ is a change in oscillating frequency, df is the change in resonant frequency, and L, M and N are constants, and $$dZ = R \times \Delta A + S$$

where $\Delta A$ is a change in amplitude, dZ is the change in resonant resistance, and R and S are constants;
wherein the constants are each derived from measurements of changes in resonant resistance and changes in resonant frequency of a plurality of viscoelastic samples whose viscoelastic characteristics are known in advance.

6. The tactile sensor signal processing device according to claim 1, wherein the piezoelectric vibrator of the tactile sensor is formed in a shape of a semi-circle.

7. The tactile sensor signal processing device according to claim 5, wherein the piezoelectric vibrator of the tactile sensor is formed in a shape of a semi-circle.

8. The tactile sensor signal processing device according to claim 1, wherein the piezoelectric vibrator of the tactile sensor is formed in a shape of a ring.

9. The tactile sensor signal processing device according to claim 5, wherein the piezoelectric vibrator of the tactile sensor is formed in a shape of a ring.

10. The tactile sensor signal processing device according to claim 1, wherein the piezoelectric vibrator of the tactile sensor is formed in a shape of a sphere.

11. The tactile sensor signal processing device according to claim 5, wherein the piezoelectric vibrator of the tactile sensor is formed in a shape of a sphere.

12. The tactile sensor signal processing device according to claim 1, wherein the piezoelectric vibrator of the tactile sensor is formed in a shape of a rectangular prism.

13. The tactile sensor signal processing device according to claim 5, wherein the piezoelectric vibrator of the tactile sensor is formed in a shape of a rectangular prism.

14. The tactile sensor signal processing device according to claim 1, wherein the piezoelectric vibrator of the tactile sensor is formed in a shape of a drainpipe.

15. The tactile sensor signal processing device according to claim 5, wherein the piezoelectric vibrator of the tactile sensor is formed in a shape of a drainpipe.

16. The tactile sensor signal processing device according to claim 1, wherein the piezoelectric vibrator of the tactile sensor is formed in a shape of a cylinder.

17. The tactile sensor signal processing device according to claim 5, wherein the piezoelectric vibrator of the tactile sensor is formed in a shape of a cylinder.

18. The tactile sensor signal processing device according to claim 1, wherein the piezoelectric vibrator of the tactile sensor is formed in a shape of a disk.

19. The tactile sensor signal processing device according to claim 5, wherein the piezoelectric vibrator of the tactile sensor is formed in a shape of a disk.

20. The tactile sensor signal processing device according to claim 1, wherein the piezoelectric vibrator of the tactile sensor is of an energy confinement type.

21. The tactile sensor signal processing device according to claim 5, wherein the piezoelectric vibrator of the tactile sensor is of an energy confinement type.

22. The tactile sensor signal processing device according to claim 1, wherein the piezoelectric vibrator of the tactile sensor has a three-terminal type of electrode structure.

23. The tactile sensor signal processing device according to claim 5, wherein the piezoelectric vibrator of the tactile sensor has a three-terminal type of electrode structure.

24. The tactile sensor signal processing device according to claim 1, wherein the piezoelectric vibrator of the tactile sensor comprises one electrode doubled as a contact which is brought into contact with the subject.

25. The tactile sensor signal processing device according to claim 5, wherein the piezoelectric vibrator of the tactile sensor comprises one electrode doubled as a contact which is brought into contact with the subject.

26. A tactile sensor signal processing device for detecting viscoelastic characteristics of a subject, comprising:
a tactile sensor that utilizes a piezoelectric vibrator;
resonant resistance change detecting means for detecting a change in resonant resistance of impedance characteristics of the piezoelectric vibrator;
resonant frequency change detecting means for detecting a change in resonant frequency of the impedance characteristics of the piezoelectric vibrator;
vibrator constant storage means for prestoring physical constants including a size of a vibrating portion of the piezoelectric vibrator, piezoelectric and coupling constants associated with a piezoelectric phenomenon of the piezoelectric vibrator, density of the piezoelectric vibrator, and a size of a contact that is pressed against the subject for applying vibrations to the subject; and
signal processing means, responsive to results of detection by the resonant resistance change detecting means and the resonant frequency change detecting means and the physical constants stored in the vibrator constant storaging means, for independently computing real and imaginary parts of shear elastic modulus indicating the viscoelastic characteristics of the subject.

27. A tactile sensor signal processing device for detecting viscoelastic characteristics of a subject, comprising:
a tactile sensor that utilizes a piezoelectric vibrator;
resonant resistance change detecting means for detecting a change in resonant resistance of impedance characteristics of the piezoelectric vibrator;
resonant frequency change detecting means for detecting a change in resonant frequency of the impedance characteristics of the piezoelectric vibrator;
vibrator constant storage means for prestoring constants involved in computation of shear elastic modulus indicating the viscoelastic characteristics of the subject; and
signal processing means, responsive to results of detection by the resonant frequency change detecting means and the resonant resistance change detecting means and the constants stored in the vibrator constant storage means, for independently computing each of a real part $\mu_1$ and an imaginary part $\mu_2$ of the shear elastic modulus of the subject based on the following two expressions:

$$df = L + M \times \Delta F^N$$

where $\Delta F$ is a change in oscillating frequency, df is the change in resonant frequency, and L, M and N are constants, and $$dZ = R \times \Delta A + S$$

where $\Delta A$ is a change in amplitude, dZ is the change in resonant resistance, and R and S are constants.

* * * * *